US008436508B2

(12) United States Patent
Kornbluh et al.

(10) Patent No.: US 8,436,508 B2
(45) Date of Patent: *May 7, 2013

(54) MECHANICAL META-MATERIALS

(75) Inventors: Roy D. Kornbluh, Palo Alto, CA (US);
Ronald E. Pelrine, Louisvillle, CO (US); Harsha Prahlad, Cupertino, CA (US); Scott E. Stanford, Mountain View, CA (US)

(73) Assignee: SRI International, Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/408,996

(22) Filed: Feb. 29, 2012

(65) Prior Publication Data
US 2012/0181896 A1 Jul. 19, 2012

Related U.S. Application Data

(60) Division of application No. 12/550,222, filed on Aug. 28, 2009, now Pat. No. 8,164,232, which is a continuation of application No. 11/078,678, filed on Mar. 11, 2005, now Pat. No. 7,598,651.

(60) Provisional application No. 60/552,456, filed on Mar. 12, 2004.

(51) Int. Cl.
*H02N 1/00* (2006.01)

(52) U.S. Cl.
USPC .......................................................... 310/309

(58) Field of Classification Search .................. 310/309, 310/326, 363; 296/180.1, 187.01; 335/78; 200/181
See application file for complete search history.

(56) References Cited

U.S. PATENT DOCUMENTS

| 2,975,307 A | 3/1961 | Schroeder et al. |
| 3,634,740 A | 1/1972 | Stevko |
| 3,916,270 A | 10/1975 | Wachtler et al. |
| 4,257,083 A | 3/1981 | Blyth |

(Continued)

FOREIGN PATENT DOCUMENTS

| GB | 2346960 | 2/1999 |
| JP | 05-253175 | 10/1993 |

(Continued)

OTHER PUBLICATIONS

Notice of Allowance dated Jan. 17, 2012 from U.S. Appl. No. 12/830,239.

(Continued)

*Primary Examiner* — Tran Nguyen
*Assistant Examiner* — Thomas Truong
(74) *Attorney, Agent, or Firm* — Beyer Law Group LLP

(57) ABSTRACT

The present invention provides meta-materials with an actively controllable mechanical property. The meta-material includes a deformable structure and a set of activation elements. The activation elements are controllable between multiple states. The meta-material includes a first value for a mechanical property when one or more of the activation elements is in the first activation state and includes a second value for the mechanical property when the activation elements have been activated to the second activation state. In one aspect, the meta-material resembles a composite material where the connectivity between the component materials or shape and arrangement of the component materials is dynamically controllable so as to affect a mechanical property of the meta-material.

11 Claims, 21 Drawing Sheets

U.S. PATENT DOCUMENTS

| | | | |
|---|---|---|---|
| 4,861,665 | A | 8/1989 | Kasahara |
| 5,206,557 | A | 4/1993 | Bobbio |
| 5,290,400 | A | 3/1994 | Bobbio |
| 5,497,861 | A | 3/1996 | Brotz et al. |
| 5,563,466 | A | 10/1996 | Rennex et al. |
| 5,638,249 | A | 6/1997 | Rubino et al. |
| 5,662,294 | A | 9/1997 | Maclean et al. |
| 5,682,075 | A | 10/1997 | Bolleman et al. |
| 5,745,331 | A | 4/1998 | Shamouilian et al. |
| 5,943,033 | A | 8/1999 | Sugahara et al. |
| 6,141,571 | A | 10/2000 | Dionne |
| 6,156,842 | A | 12/2000 | Hoenig et al. |
| 6,184,608 | B1 | 2/2001 | Cabuz et al. |
| 6,198,204 | B1 | 3/2001 | Pottenger |
| 6,376,971 | B1 | 4/2002 | Pelrine et al. |
| 6,388,043 | B1 | 5/2002 | Langer et al. |
| 6,420,814 | B1 | 7/2002 | Bobbio |
| 6,485,273 | B1 | 11/2002 | Goodwin-Johansson |
| 6,514,895 | B1 | 2/2003 | Chiu et al. |
| 6,519,074 | B2 | 2/2003 | Little et al. |
| 6,646,364 | B1 | 11/2003 | Horning et al. |
| 6,646,525 | B2 | 11/2003 | Bozler et al. |
| 6,683,516 | B2 | 1/2004 | Chiu et al. |
| 6,684,469 | B2 | 2/2004 | Horning et al. |
| 6,693,790 | B2 | 2/2004 | Matsuki et al. |
| 6,709,739 | B1 | 3/2004 | Mullen et al. |
| 6,760,214 | B2 | 7/2004 | Tomaru et al. |
| 6,774,077 | B2 | 8/2004 | Sengupta et al. |
| 6,781,284 | B1 | 8/2004 | Pelrine et al. |
| 6,781,812 | B2 | 8/2004 | Fuwa et al. |
| 6,791,817 | B2 | 9/2004 | Allison et al. |
| 6,793,937 | B2 | 9/2004 | Quong |
| 6,795,296 | B1 | 9/2004 | Palanduz et al. |
| 6,812,624 | B1 | 11/2004 | Pei et al. |
| 6,813,064 | B2 | 11/2004 | John et al. |
| 6,876,279 | B2 | 4/2005 | Sengupta et al. |
| 6,882,086 | B2 | 4/2005 | Kornbluh et al. |
| 6,905,989 | B2 | 6/2005 | Ellis et al. |
| 6,907,294 | B2 | 6/2005 | Andino et al. |
| 7,053,737 | B2 | 5/2006 | Schwartz et al. |
| 7,105,758 | B2 | 9/2006 | Nakanishi et al. |
| 7,196,599 | B2 | 3/2007 | Dabbaj |
| 7,218,191 | B2 * | 5/2007 | Bozler et al. ............. 333/262 |
| 7,256,670 | B2 | 8/2007 | Jahnes et al. |
| 7,283,024 | B2 * | 10/2007 | Bar et al. ............. 335/78 |
| 7,372,690 | B2 | 5/2008 | Moffatt |
| 7,551,419 | B2 | 6/2009 | Pelrine et al. |
| 7,554,787 | B2 | 6/2009 | Pelrine et al. |
| 7,598,651 | B2 | 10/2009 | Kornbluh et al. |
| 7,598,652 | B2 | 10/2009 | Kornbluh et al. |
| 7,669,918 | B2 | 3/2010 | Buravalla et al. |
| 7,773,363 | B2 | 8/2010 | Pelrine et al. |
| 7,872,850 | B2 | 1/2011 | Pelrine et al. |
| 8,111,500 | B2 | 2/2012 | Pelrine et al. |
| 8,125,758 | B2 | 2/2012 | Pelrine et al. |
| 8,164,232 | B2 | 4/2012 | Kornbluh et al. |
| 2002/0082668 | A1 | 6/2002 | Ingman |
| 2002/0166212 | A1 | 11/2002 | Pratl |
| 2002/0191267 | A1 | 12/2002 | Flanders et al. |
| 2003/0184731 | A1 | 10/2003 | Allison et al. |
| 2004/0056742 | A1 | 3/2004 | Dabbaj |
| 2005/0235537 | A1 | 10/2005 | Robert Lee et al. |
| 2006/0186700 | A1 | 8/2006 | Browne et al. |
| 2006/0192465 | A1 | 8/2006 | Kornbluh et al. |
| 2007/0024403 | A1 | 2/2007 | Kwon et al. |
| 2007/0285870 | A1 | 12/2007 | Shim |
| 2008/0075930 | A1 | 3/2008 | Kornbluh et al. |
| 2009/0028670 | A1 | 1/2009 | Garcia et al. |
| 2010/0007240 | A1 | 1/2010 | Kornbluh et al. |
| 2010/0249553 | A1 | 9/2010 | MacLaughlin |
| 2012/0120544 | A1 | 5/2012 | Pelrine et al. |

FOREIGN PATENT DOCUMENTS

| | | |
|---|---|---|
| JP | 6-341489 | 12/1994 |
| JP | 5-344753 | 12/1996 |
| JP | 2003-506858 | 2/2003 |
| WO | 7900510 | 8/1979 |
| WO | 9420984 | 9/1994 |

OTHER PUBLICATIONS

Notice of Allowance dated Nov. 28, 2011 from U.S. Appl. No. 12/964,614.

Office Action dated Jun. 10, 2011 from U.S. Appl. No. 12/964,614.

Chinese Office Action dated Dec. 2, 2010 from Chinese Application No. 200580014841.7.

Office action dated Aug. 8, 2011 from Chinese Application No. 200580014841.7.

Office Action dated Apr. 4, 2011 from U.S. Appl. No. 12/830,239.

Final Office Action dated Aug. 23, 2011 from U.S. Appl. No. 12/830,239.

Office Action dated Feb. 1, 2011 from Japanese Application No. 2007-502971.

Office Action dated Nov. 5, 2010 from U.S. Appl. No. 12/550,222.

Final Office Action dated Apr. 21, 2011 from U.S. Appl. No. 12/550,222.

Notice of Allowance dated Sep. 20, 2010 in U.S. Appl. No. 12/467,080.

Longo et al., "Control Architecture for the Alicia3 Climbing Robot", Proceedings of the World Automation Congress 2004, Seville Spain, Jun. 2004, pp. 419-424.

Xu et al., "A Wall Climbing Robot for Labelling Scale of Oil Tank's Volume", Robotica, vol. 20, pp. 209-212, Mar. 2002.

DARPA, "Defense Funds 36 Urban Warfighting Technology Projects", News Release, Defense Advanced Research Projects agency, Dec. 17, 2004.

Yamamoto et al., "Wall Climbing Mechanisms Using Electrostatic Attraction Generated by Flexible Electrodes," Micro-NanoMechatronics and Human Science, 2007. MHS '07. International Symposium on <http://ieeexplore.ieee.org/xpl/RecentCon.jsp?punumber=4420810> Nov. 11-14, 2007 pp. 389-394 Digital Object Identifier 10.1109/MHS.2007.4420886.

Andeen et al., 1988. "Design of Compliance in Robotics," Proc. IEEE Conference on Robotics and Automation, Philadelphia, Pennsylvania, pp. 276-281.

Ashley, S., "Smart Skis and Other Adaptive Structures", Mechanical Engineering, Nov. 1995, pp. 77-81.

Bakshaev, G.I., "RK, LIG-7" from http://www.ctrl-c.liu.se/misc/ram/rk.html on Feb. 1, 2005.

Bar-Cohen, Y., (ed.), Electroactive Polymer (EAP) Actuators as Artificial Muscles-Reality, Potential and Challenges, SPIE Press, Bellingham, Washington, 2001.

Baughman et al., "Conducting polymer electromechanical actuators," Conjugated Polymeric Materials: Opportunities in Electronics, Optoelectronics and Molecular Electronics, eds. J. Bredas and R. Chance, Kluwer Academic Publishers, The Netherlands, pp. 559-582, 1990.

Bergamini et al., "Electrostatic Tuning of the Bending Stiffness of Simple, Slender Multi-layer Composite Structures," SPIE Annual International Symposium on Smart Structures and Materials 2005, San Diego, Mar. 7, 2005, vol. 5760, pp. 152-162.

Blaya, "Force Controllable Ankle-Foot Orthosis (AFO) to Assist Drop Foot Gait," Dept. of Mechanical Engineering Masters Thesis, Cambridge, MA: Massachusetts Institute of Technology, 2002.

Bobbio et al., "Integrated force arrays," Proc. IEEE Micro Electro Mechanical Systems Workshop, Fort Lauderdale, Florida, 1993.

Carpenter et al., "Equilibrium and Transient Studies of Mechanical Properties of 1,2-Polybutadiene Cross-Linked in Simple Extension," Journal of Rheology, Abstracts of the 48$^{th}$ Meeting, vol. 23, 1979.

Dunne et al., "Ground Demonstration of the Smart Inlet," AIAA 2000-1630, in 41$^{st}$ Structures, Structural Dynamics, and Materials Conference and Exhibit Adaptive Structures Forum, Atlanta, GA (Apr.).

Ferry et al., "Interpretation of Deviations From Neo-Hookean Elasticity by a Two-Network Model with Crosslinks and Trapped Entanglements," Rubber Chemistry and Technology, vol. 51, 730-737, Mar. 1978.

Ferry, John D., "Applications of a two-network model for crosslinks and trapped entanglements," Polymer, 1979, vol. 20, Nov.

Ginder et al. "Controllable-stiffness components based on magnetorheological elastomers," Smart Structures and Materials 2000: Smart Structures and Integrated Systems, Proc. SPIE vol. 3985, pp. 418-425 (2000).

Goldfarb, "Control for a Self-Contained Microcomputer-Controlled Above-Knee Prosthesis," Department of Mechanical Engineering Masters Thesis, Cambridge, MA: Massachusetts Institute of Technology, 1992.

Granick et al., "Entangled Chain Structure Trapped in a Styrene-Butadiene Random Copolymer by Cross-Linking in Simple Extension," Macromolecules 1983, 16, 39-45.

Hawkins et al., "Machine Augmented Composites", in Smart Structures and Materials 2002: Industrial and Commercial Applications of Smart Structures Technologies, ed. A.R. McGowen, Proc. SPIE, vol. 4698, pp. 231-236 (2002).

Herr, H., "Presentation highlights: Prosthetic and orthotic limbs", Journal of Rehabilitation Research and Development, vol. 39, No. 3 (Supplement), May/Jun. 2002, VA/NIH Prosthetics Roundtable, pp. 11-12 (2002).

Hodgson et al., "Shape Memory Alloys", From Metals Handbook, vol. 2, Tenth Edition.

Hunter et al., "A comparison of muscle with artificial actuators," Tech. Digest of IEEE Solid-State Sensor and Actuator Workshop, Hilton Head, South Carolina, pp. 178-185, 1992.

Hunter et al., "Fast reversible NiTi fibers for use in microrobotics," Proc. 1991 IEEE Micro Electro Mechanical Systems-MEMS '91, Nara, Japan, pp. 166-170, 1991.

Hvidt et al., "Contribution of Entanglements to the Equilibrium Modulus of 1,2-Polybutadiene Networks at Small Strains and Estimate of the Front Factor," Macromolecules 1980, 933-939.

Kan et al., "Trapped Entanglements vs. Dissociable Junctions in Networks Cross-Linked in Strained States," Macromolecules 1980, 13, 1313-1314.

Kornbluh et al., "Application of Dielectric EAP Actuators," Electroactive Polymer (EAP) Actuators as Artificial Muscles-Reality, Potential and Challenges, ed. Y. Bar-Cohen, SPIE Press, Bellingham, Washington, pp. 457-495, 2001.

Kornbluh et al., "Electroelastomers: applications of dielectric elastomer transducers for actuation, generation and smart structures," Smart Structures and Materials 2002: Industrial and Commercial Applications of Smart Structures Technologies, ed. A. McGowan, Proc. SPIE 4698, pp. 254-270, 2002.

Kornbluh et al., "Rubber to rigid, clamped to undamped: Toward composite materials with wide-range controllable stiffness and damping," SPIE Smart Structures and Materials 2004: Industrial and Commercial Applications of Smart Structures Technologies, San Diego, Mar. 2004.

Kornbluh et al., "Rubber to Rigid: Composite Structures with Electronically Controllable Stiffness and Damping," SPIE Smart Structures and Materials 2004: Industrial and Commercial Applications of Smart Structures Technologies, San Diego, Mar. 2004.

Kornbluh et al., Slide presentation, "Rubber to rigid, clamped to undamped: Toward composite materials with wide-range controllable stiffness and damping," SPIE Smart Structures and Materials 2004: Industrial and Commercial Applications of Smart Structures Technologies, San Diego, Mar. 14, 2004.

Kudva et al., Overview of the DARPA/AFRL/NASA Smart Wing Phase 2 Program, Smart Structures and Materials, 2001, Industrial and Commercial Applications of Smart Structures Technolohies, Proceedings of SPIE vol. 4332 (2001).

Lampe, Materials Database on Commercially Available Electro-and Magnetorheological Fluids (ERF and MRF), available at http://www.tu-dresden.de/mw/ilr/lampe/HAUENG.HTM (1997).

Liu et al., "Tailored Shape Memory Polymers: Not all SMPs are Created Equal," Proceedings of The First World Congress on Biomimetics, Dec. 9-11, 2002, Albuquerque, NM.

Machida et al., "Vibration control by smart structure with electrorheological fluid", in Smart Structures and Materials 2001: Smart Structures and Integrated Systems, L. Porter Davis, ed., Proc. of the SPIE vol. 4327, pp. 176-184. (2001).

Madden et al., "Artificial Muscle Technology: Physical Principals and Naval Prospects", IEEE Journal of Oceanic Engineering, Special Issue on Biorobotics, accepted for publication (2004).

Maly et al., "Complex Stiffness Measurement of Vibration-Damped Structural Elements," Presented at the International ModalAnalysis Conference, IMAC-XVIII, San Antonio, Texas, Feb. 2000.

McGowan et al., "Recent Results from NASA's Morphing Project", in Smart Structures and Materials 2002: Industrial and Commercial Applications of Smart Structures Technologies, ed. A.R. McGowen, Proc. SPIE 4698, pp. 254-270, 2002.

McKnight et al., "Investigating the Passive Damping Properties of Active Materials," Mechanical and Aerospace Engineering Department, University of California, Los Angeles.

Mercier Des Rochettes et al., "Materials and actuators for the shape control of structures", in Smart Structures and Materials 2001: Smart Structures and Integrated Systems, L. Porter Davis, Editor, Proceedings of the SPIE vol. 4327, pp. 67-78 (2001).

Murray, William M., "GB-154 Smart Materials: Technology Assessment Patent Review/Market Potential," from http://www.bc-cresearch.com/archive/GB154.html on Jul. 26, 2005.

NewScientist.com news service, "The next 100 years of flight—part two," Dec. 17, 2003.

Park et al., "Ultrahigh strain and piezoelectric behavior in relaxor based ferroelectric single crystals," J. Applied Physics 82, pp. 1804-1811, 1997.

Pelrine et al., "Dielectric Elastomers: Generator Mode Fundamentals and Applications," in Smart Structures and Materials 2001: Electroactive Polymer Actuators and Devices, ed. Y. Bar-Cohen, Proc. SPIE 4329, pp. 148-156, 2001.

Pelrine et al., "High Speed Electrically Actuated Elastomers with Over 100% Strain," Science 287:5454, pp. 836-839, 2000.

Pelrine et al., "High-Strain Actuator Materials Based on Dielectric Elastomers," Advanced Materials 2000 12:16, pp. 1223-1225, 2000.

Pornsin-Sirirak et al. "MEMS Wing Technology for a Battery-Powered Ornithopter," The 13th IEEE International Conference on Micro Electro Mechanical Systems (MEMS '00), Miyazaki, Japan, Jan. 23-27, 2000, pp. 799-804.

Pornsin-Sirirak et al., "Flexible Parylene Actuator for Micro Adaptive Flow Control," The 14th IEEE International MEMS Conference (MEMS '01), Interlaken, Switzerland, Jan. 21-25, 2001, pp. 511-514.

Pornsin-Sirirak et al., "Flexible Parylene-Valved Skin for Adaptive Flow Control," The 15th IEEE International MEMS Conference (MEMS '02), Las Vegas, U.S.A., Jan. 20-24, 2002.

Pornsin-Sirirak et al., "Titanium-Alloy MEMS Wing Technology for a Micro Aerial Vehicle Application," Sensors and Actuators, A: Physical, vol. 89, Issue 1-2, Mar. 20, 2001, pp. 95-103.

Pornsin-Sirirak et al., "Unsteady-state Aerodynamic Performance of MEMS Wings," International Symposium on Smart Structure and Microsystems 2000 (IS3M 2000), The Jockey Club, Hong Kong, Oct. 19-21, 2000.

Prock et al., "Morphing Airfoil Shape Change Optimization with Minimum Actuator Energy as an Objective," 9th AIAA/ISSMO Symposium on Multidisciplinary Analysis and Optimization, Atlanta, GA Sep.4.

Shahinpoor, M., "Micro-electro-mechanics of ionic polymer gels as electrically controllable artificial muscles," J. Intelligent Material Systems and Structures 6, pp. 307-314, 1995.

Simpson et al., "Innovative Materials for Aircraft Morphing," Materials Division, NASA Langley Research Center.

Sproston et al., "Controllable Fluids in 2002-Status of ER and MR Fluid Technology," Proc. Actuator 2002, 8th International Conf. on New Actuators, Bremen, Germany (Jun.), pp. 333-338, 2002.

SRI International, DARPA Proposal, "Electrostatic Materials for Tentacles and Reconfigurable Space Structures," Jun. 18, 2004.

SRI International, DARPA Proposal, "Electrostatic Materials for Tentacles and Reconfigurable Space Structures," Quarterly Report, Jan. 2005.

Tobushi et al., "Mechanical properties of shape memory polymer of polyurethane series," JSME International J., Series I, 35:3, 1992.

University of Maryland presentation, "Shape Memory Materials," Mar. 1, 2004.

Unsal et al., "A New Semi-Active Piezoelectric-Based Friction Damper", in Proceedings of SPIE vol. 5052 Smart Structures and

*Materials 2003: Damping and Isolation*, ed. G. Agnes, K. Wang (SPIE Bellingham, WA), pp. 413-420 (2003).
Wolons et al., "An Experimental Investigation of the Pseudoelastic Hysteresis Damping Characteristics of Nickel Titanium Shape Memory Alloy Wires," in Proceedings of the AIAA/ASME/ASCE/AHS/ASC Structures, Structural Dynamics, and Materials Conference and Exhibit, 39th, and AIAA/ASME/AHS/ Adaptive Structures Forum, Long Beach, CA, Apr. 20-23, 1998, AIAA Paper 98-2036 (1998).
Xia et al., "Poly(vinylidene fluoride-trifluoroethylene) based high performance electroactive polymers," *Smart Structures and Materials 2003. Electroactive Polymer Actuators and Devices (EAPAD)*, ed. Y. Bar-Cohen, *Proc. SPIE* 5051, pp. 133-142, 2003.
Krape et al., "Applications Study of Electroadhesive Devices," Prepared under Contract No. NAS 1-7303 by Chrysler Corporation Space Division, New Orleans, La., National Aeronautics and Space Administration, Oct. 1968.
Sommer-Larsen et al., "Polymer Actuators," *Proc. Actuator 2002, 8th International Conf. on New Actuators*, Bremen, Germany (Jun.), pp. 371-378, 2002.
Rao et al., "Baverstam Associates' Electronic Newsletter Q2 2003, vol. #3, Issue #2.".
Presentation to DARPA DSO officials on May 26, 2006 entitled "Electroadhesive Wall-Climbing Robot for Three-Dimensional Mobility in Urban Environments.".
Office Action dated Apr. 17, 2007 in U.S. Appl. No. 11/078,678.
Office Action dated Nov. 6, 2007 in U.S. Appl. No. 11/078,678.
Office Action dated Apr. 29, 2008 in U.S. Appl. No. 11/078,678.
International Search Report dated Jul. 30, 2008 in PCT Application No. PCT/US07/70432.
Written Opinion dated Jul. 30, 2008 in PCT Application No. PCT/US07/70432.
Office Action dated Aug. 7, 2008 in U.S. Appl. No. 11/757,913.
International Search Report dated Aug. 15, 2008 in PCT Application No. PCT/US07/70437.
Written Opinion dated Aug. 15, 2008 in PCT Application No. PCT/US07/70437.
Office Action dated Dec. 3, 2008 in U.S. Appl. No. 11/078,678.
Office Action dated Dec. 3, 2008 in U.S. Appl. No. 11/830,806.
Notice of Allowance dated Apr. 3, 2009 in U.S. Appl. No. 11/757,913.
Notice of Allowance dated Apr. 24, 2009 in U.S. Appl. No. 11/757,922.
Office Action dated May 11, 2009 in U.S. Appl. No. 11/078,678.
Office Action dated May 13, 2009 in U.S. Appl. No. 11/830,806.
Supplemental Notice of Allowance dated May 15, 2009 in U.S. Appl. No. 11/757,913.
Notice of Allowance dated Aug. 17, 2009 in U.S. Appl. No. 11/830,806.
Notice of Allowance dated Aug. 18, 2009 in U.S. Appl. No. 11/078,678.
Office Action dated Nov. 27, 2009 in Chinese Application No. 200580014841.7.
Notice of Allowance dated Apr. 7, 2010 for U.S. Appl. No. 11/830,814.
Carpenter et al., "Entanglement Networks of 1,2-Polybutadiene Cross-Linked in States of Strain. V. Relaxation Phenomena and Calculations of Entanglement Trapping," Polymer Engineering and Science, vol. 19, No. 4, Mar. 1979.
Carpenter et al., "Entanglement Networks of 1,2-Polybutadiene Crosslinked in States of Strain. IX. Swelling and Anisotropy," Journal of Polymer Science: Polymer Physics Edition, vol. 18, 615-167 (1980).
Carpenter et al., "Entanglement Networks of 1,2-Polybutadiene CrossLinked in States of Strain. IV. States of Ease and Stress-Strain Behavior," Journal of Applied Polymer Science, vol. 22, pp. 335-342 (1978).
Carpenter et al., "Entanglement Networks of 1,2-Polybutadiene Cross-Linked in States of Strain. 3. Effect of Temperature," Macromolecules, vol. 10, No. 1, Jan.-Feb. 1977.
Kan et al., "Entanglement Networks of 1,2-Polybutadiene Crosslinked in States of Strain.VII. Stress-Birefringence Relations," Journal of Polymer Science: Polymer Physics Edition, vol. 17, 1855-1869 (1979).
Kan et al., "Entanglement Networks of 1,2-Polybutadiene Crosslinked in States of Strain, 8. Trapping of Entanglements in Relaxed and Unrelaxed Configurations," Macromolecules, vol. 12, No. 3, 494-498, May-Jun. 1979.
Kan et al., "Stress-Birefringence Relations in Networks of 1,2-Polybutadiene Cross-Linked in Uniaxial Extension," Journal of Rheology, vol. 23, Issue 3, Jun. 1979.
Kramer et al., "Entanglement Networks of 1,2-Polybutadiene Cross-Linked in States of Strain. I. Cross-Linking at 0°," Macromolecules, vol. 7, No. 1, Jan.-Feb. 1974.
Kramer et al., "Entanglement Networks of 1,2-Polybutadiene Crosslinked in States of Equibiaxial Extension," Journal of Polymer Science: Polymer Physics Edition, vol. 15, pp. 761-763 (1977).
Office Action dated Jan. 31, 2012 from Japanese Application No. 2007-502971.
Notice of Allowance dated Feb. 16, 2012 from U.S. Appl. No. 12/550,222.

* cited by examiner

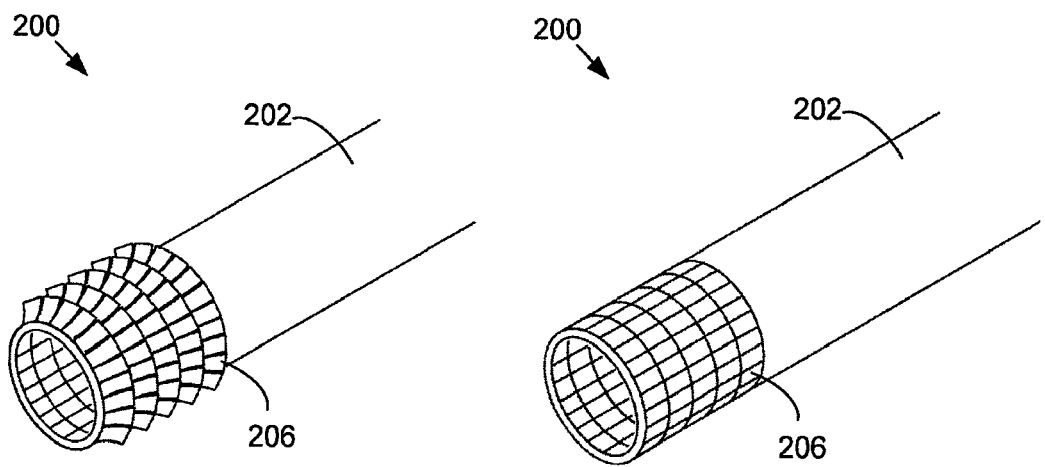
FIG. 2K          FIG. 2L magnetic input

MECHANICAL META-MATERIALS

CROSS-REFERENCE TO RELATED APPLICATIONS

This application is a divisional of and claims priority from and commonly owned U.S. patent application Ser. No. 12/550,222, filed Aug. 28, 2009 now U.S. Pat. No. 8,164,232 and entitled "Mechanical Meta-Materials," which is a continuation of and claims priority from U.S. patent application Ser. No. 11/078,678, filed Mar. 11, 2005 and entitled "Mechanical Meta-Materials," which is now U.S. Pat. No. 7,598,651, and which in turn claims priority from U.S. Provisional Patent Application No. 60/552,456, filed Mar. 12, 2004, all of which are incorporated by reference in their entirety and for all purposes.

U.S. GOVERNMENT RIGHTS

This application was made in part with government support under contract number FA8650-04-C-7140 awarded by the United States Air Force Research Laboratory and Defense Advanced Research Project Agency. The government has certain rights in the invention.

BACKGROUND

This invention relates to a composite material having a controllable mechanical property. More particularly, the invention relates to a composite meta-material with a property that may be altered after fabrication and during usage.

Historically, man was initially limited in materials selection to what was available around him: wood, stones and bones. He eventually gained the ability to refine naturally occurring materials such as iron and bronze and to mold and shape these materials. A few millennia later, man invented custom materials and composites, such as plastics and reinforced steel, whose mechanical properties could be tailored during fabrication for a specific application.

Revolutions in materials technology led to applications revolutions. The Iron and Bronze Ages produced shaped weapons, farm tools, jewelry, and eating utensils. Composite materials at the turn of the 20th-century enabled a wide array of new applications. Flight leveraged new lightweight and high strength materials; steel-reinforced concrete built bigger buildings and bridges; and plastics led to revolutions in toys and other industries.

These materials allowed the designer or builder to select from a wide range of mechanical properties for a given application. However, once the material is selected and incorporated into a device or structure, its mechanical properties are fixed. The ability to actively control a mechanical property of a material during usage would be useful in many applications—and enable many new ones. Existing materials that can vary a mechanical property are still very limited and may be divided into two categories: active materials and intrinsically adaptive materials.

Intrinsically adaptive materials undergo transformations in their molecular or microscopic structure in response to external stimuli, which results in a mechanical property change. Examples of intrinsically adaptive materials include thermally responsive materials, such as rubber and shape memory polymers, where stiffness and damping vary based on temperature; magentorheological and electrorheological fluids where the material undergoes a microstructural transformation in response to an external magnetic or electric field; and polymer gels where the stiffness changes depending on the amount of fluid in the polymeric matrix. These materials can exhibit undesirable temperature sensitivity. Also, these materials provide limited control. For example, it is not possible to independently vary elasticity and damping for these materials or to control an electrorheological fluid between liquid/solid extremes.

Active materials act as energy transducers that convert between electrical (or thermal) energy and mechanical energy of deformation. Examples of active materials include piezoelectric ceramics, magnetostrictive materials (including ferromagnetic shape memory alloys), and electroactive polymers. For these materials, their particular energy conversion mechanism often limits the range of mechanical properties that can be obtained. In addition, control of a mechanical property for an active material is subject to physical limits, such as maximum energy output and speed of response for the active material.

Based on the foregoing, materials selection is still limited and materials with one or more controllable mechanical properties largely remain an unmet need.

SUMMARY

The present invention provides meta-materials with an actively controllable mechanical property. The meta-material includes a deformable or reconfigurable structure and a set of activation elements. The activation elements are controllable between multiple states. The meta-material includes a first value for a mechanical property when one or more of the activation elements is in the first activation state and includes a second value for the mechanical property when the activation elements have been activated to the second activation state. In one aspect, the meta-material resembles a composite material whose structure or connectivity is controllable so as to affect a mechanical property of the meta-material.

One exemplary meta-material includes a compliant layer as the deformable structure and a set of rigid activation elements coupled to the compliant layer. Each rigid activation element may be electrostatically clamped to another rigid activation element or to the compliant layer so as to increase its coupling to another rigid activation element. This changes connectivity of the meta-material. When multiple activation elements are clamped (activated) together, the meta-material increases in stiffness, damping or another mechanical property. When clamping is turned off (de-activation), the meta-material mechanically resembles the compliant layer. Correspondingly, stiffness or another mechanical property for this meta-material may be controlled to range from nearly that of the compliant layer to that of the rigid material when all the activation elements are electrostatically clamped.

These controllable meta-materials find wide use. For example, meta-materials may be included in a device enabling tunable impedance. The composites can also be multifunctional materials: they can minimize size and mass by acting both as controllable mechanical components and as supporting structures. One such multifunctional use is a robotic or vehicular skin that is protective, adaptive and functional (e.g., energy absorbing).

In one aspect, the present invention relates to a meta-material. The meta-material includes a deformable or reconfigurable structure (henceforth referred to as a deformable structure for simplicity) and a set of activation elements. Each activation element a) couples to the deformable structure, b) includes a component that participates in an activation mechanism, and c) is configured to change between a first activation state and a second activation state. The meta-material includes a first value for a mechanical property when at least one of the activation elements is in the first activation state and includes a second value for the mechanical property when the at least one activation element has been activated to the second activation state.

In another aspect, the present invention relates to a meta-material that offers stiffness control. The meta-material includes a deformable structure and a set of activation elements. Each activation element a) couples to the deformable structure, b) includes a relatively stiff component, and c) is configured to change between a first activation state and a second activation state. The meta-material includes a first stiffness when at least one of the activation elements is in the first activation state and the meta-material includes a second stiffness when the at least one activation element has been activated to the second activation state.

In yet another aspect, the present invention relates to a meta-material that offers damping control. The meta-material includes a first damping coefficient when at least one of the activation elements is in the first activation state and the meta-material includes a second damping coefficient when the at least one activation element has been activated to the second activation state.

In still another aspect, the present invention relates to an electrostatically clamping meta-material. The meta-material includes a deformable structure and a set of activation elements. Each activation element includes a stiff component that couples to the deformable structure. The meta-material includes a first value for a mechanical property when at least one of the activation elements is not electrostatically clamped to another activation element and the meta-material includes a second value for the mechanical property when the at least one activation element has been electrostatically clamped to another activation element.

In another aspect, the present invention relates to a method of controlling a mechanical property for a meta-material. The method comprises activating at least one activation element from a first activation state to a second activation state. The meta-material includes a first value for the mechanical property when the at least one activation element is in the first activation state and includes a second value for the mechanical property when the at least one activation element has been activated to the second activation state.

In yet another aspect, the present invention relates to a method of varying stiffness using a meta-material. The method comprises activating at least one activation element from a first activation state to a second activation state. The at least one activation element includes a modulus of elasticity greater than that of the deformable structure. The meta-material includes a first stiffness when the at least one activation element is in the first activation state and the meta-material includes a second stiffness when the at least one activation element has been activated to the second activation state.

In still another aspect, the present invention relates to a method of changing shape of a meta-material. The method comprises at least partially de-activating one or more activation elements. The method also comprises applying a force to the deformable structure such that the meta-material acquires a new shape. The method further comprises activating the one or more activation elements when the meta-material acquires the new shape.

In another aspect, the present invention relates to a method absorbing energy using a meta-material. The method comprises activating at least one activation element from a first activation state to a second activation state. The meta-material includes a first value for a mechanical property when the at least one activation element is in the first activation state and includes a second value for the mechanical property when the at least one activation element has been activated to the second activation state. The method further comprises applying a force to the meta-material such that the deformable structure deforms.

These and other features and advantages of the present invention will be described in the following description of the invention and associated figures.

BRIEF DESCRIPTION OF THE DRAWINGS

FIGS. 2K and 2L illustrate a meta-material disposed in a cylindrical topology in accordance with one embodiment of the present invention.

DETAILED DESCRIPTION

The present invention is described in detail with reference to a few preferred embodiments as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

Overview

A meta-material includes a controllable mechanical property. The mechanical property may be dynamically changed during usage—after production or fabrication. A meta-material is similar to a conventional composite in that it includes more than one material component. However, a meta-material of the present invention incorporates a controllable element that may be dynamically activated.

Figure 7A:
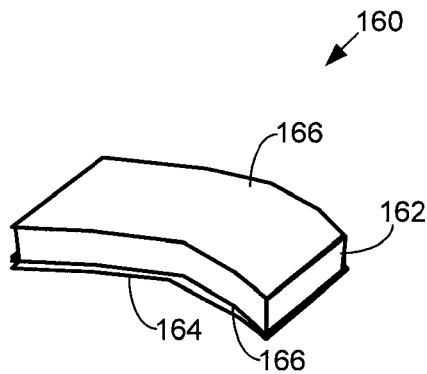
FIG. 7A illustrates an activation element of a meta-material that uses and locks in a shape change to increase stiffness in accordance with a specific embodiment of the present invention.
Figure 7B:
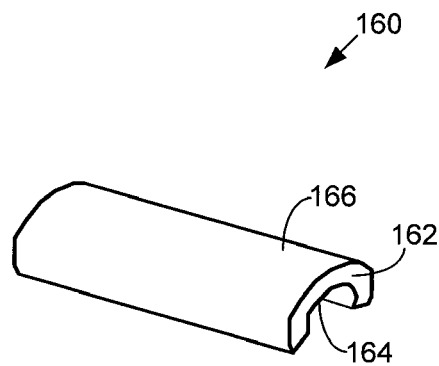
FIG. 7B shows the activation element of FIG. 7A after activation.

The meta-material includes a deformable or reconfigurable structure and a set of activation elements. The deformable structure may include a single material or a more complex structure including multiple components. One simpler deformable structure is a compliant sheet. In this case, deactivation of all the activation elements causes the meta-material to substantially resemble mechanical properties of the compliant sheet. A complex structure may include multiple components that interact to form a single operable mechanism (e.g., a fibrous weave of FIG. 11 or the structures FIGS. 4-5). In shape changing embodiments, the deformable structure includes enough compliance to be responsive to external forces responsible for the shape change. Some deformable structures include a design where shape of the structure affects a mechanical property of the meta-material (FIGS. 7A-7B).

Activation of one or more of the activation elements alters the mechanical property of interest. In one embodiment, the activation elements are separate individual structures coupled to the deformable structure, such as high stiffness and overlapping 'scales' on a compliant sheet (FIGS. 2A-2L). In another embodiment, the activation elements are portions of a common material combined with the deformable structure, such as separably controllable active areas on an electroactive polymer.

The deformable structure may include an existing structure and does not need to be a separate element that is unique to the meta-material. An example is given below where scales are disposed on the surface of a tentacle. In this case the deformable structure is the tentacle itself. The deformable structure need not be a passive material or structure. Alternatively, it can include active materials that undergo shape change or induce forces upon electrical stimulation for example. For example, the deformable structure could be a sheet of electroactive polymer that expands in response to the application of a suitable voltage. In another example, the deformable structure could be an electrostatic motor where two relatively rigid sheets slide past each other in response to electrical stimulation.

The activation elements in a meta-material employ an activation mechanism. In general, the activation mechanism may employ any suitable method or system for controllably altering a mechanical property of a meta-material. In one embodiment, the activation mechanism is electrostatic clamping, where two conductive surfaces are clamped together due to electrostatic forces created by an applied electric field. In another embodiment, the activation mechanism may include mechanical clamping, where two components or surfaces clamp together and lock in place due to mechanical forces induced by levers, springs, or other means that operate in a direction separate from an external load. Activation elements that respond to magnetic input to change a mechanical property of the meta-material are also described. The activation mechanism may include other techniques. Some examples include electromagnetics (for example, solenoids or motors), piezoelectrics, electroactive polymers, shape memory alloys, metals and other materials that change size or shape with temperature, polymer gels that change size in response to electrical stimulation or chemical gradient, bladders, cylinder or other chambers that change shape in response to fluid that is added or removed from the chamber, and electrorheological or magnetorheological fluids located between two rigid elements or within a deformable cell, or any other actuator that can move a clamping mechanism. The controllable element may also include active or intrinsically variable materials and their respective activation mechanisms. A meta-material can also include other activation mechanisms that are not stand-alone materials, such as electrostatically or electromagnetically induced clamping or motion. In some cases, the activation elements may combine two or more of these mechanisms. For example, mechanical locking may be combined with electrostatic or electromagnetic actuation.

The activation elements are configured to change between activation states. The meta-material's mechanical property changes with different activation states of one or more activation elements. For electrostatic clamping, the activation states may include unclamped, fully clamped and partially clamped. For mechanical clamping, activation states may include mechanically locked, free, and frictionally related. Magnetic activation may include magnetic states similar to electrostatic clamping or mechanical clamping. In addition, it may include permanent magnetic force as created by permanent magnets. Different positions of an activation element may also convey different states. In general, the activation states will vary with the particular activation mechanism, as one of skill in the art will appreciate.

In one embodiment, the activation elements change connectivity of the meta-material when activated. This may include changing connectivity between activation elements and/or changing connectivity between the activation elements and the deformable structure. This change of connectivity need not involve a large deformation of the structure and thus we say that the structure may alternatively be reconfigurable instead of deformable. An example of a change in connectivity between activation elements is provided below where honeycomb structures are discussed (e.g. FIG. 4). The honeycomb is comprised of an array of interconnected kinematic mechanisms with relatively rigid sides flexible joints. When not in the activated state, the mechanisms are free to move. However, in one embodiment, electrostatic clamping creates a new rigid side element that divides the mechanism into two truss-like structures that cannot deform in response to an external load. This is referred to as a change in connectivity because all of the elements of the structure are there, but by activation we can connect elements and greatly change the mechanical response of the structure.

An example of a change in connectivity between activation elements and the deformable structure is provided below (e.g. FIGS. 1 and 2). In this case the activation changes the connection between the deformable structure and the rigid elements. In one state the deformable structure is connected to the external load, making the material appear low-stiffness. In another state the rigid elements are now connected to the deformable structure, which in turn is connected to the external load thereby making the material appear stiff.

A meta-material is considered herein as a composite and sufficiently homogenous to be a material rather than a collection of easily separable subsystems. In one sense, the set of activation elements collectively forms one material in the composite, and the meta-material is considered a composite material where one of the materials in the composite is externally controllable. Some composites include a "meso-scale" structure that can be actively changed to modulate a mechanical property. "Meso-scale" is defined here to be greater than molecular scale, but smaller than the macroscopic scale of interest in an application. In some cases meso-scale features can be quite small and produced by microfabrication techniques. In other cases, they can be large (such as inches). The meso-scale meta-material is sized such that its activation elements are small compared to the important characteristic size of the overall meta-material (such as the overall thickness, length, or amount of deformation).

One advantage of the present invention is that it is scale invariant. For example, planar designs where rigid activation elements are coupled to a compliant structure may be implemented in a wide range of sizes. In one embodiment, the activation elements are large and in the range of several inches. In another embodiment, the activation elements are minute and not readily visible to the human eye. Thus, principles and components for several embodiments described herein work regardless of size for the activation elements and deformable structure. Many meta-materials described herein may be implemented on both the micro (less than 1 mm) and macro (greater than 1 mm) level.

Mechanical properties that may be dynamically altered for a meta-material of the present invention include stiffness, damping, rigidity, toughness, resilience, and elastic modulus. Other mechanical properties, as well as the overall shape may also be controlled, and several are described below.

Similar to existing composites (e.g., reinforced concrete) whose individual materials (concrete and steel) are selected for their individual desired properties (compressive and tensile strength, respectively), mechanical properties of a meta-material may also be tailored and selected during design and fabrication. The present invention, however, provides another degree-of-freedom to materials selection: ingredients used in a meta-material may also be selected during design and fabrication according to their ability to dynamically produce changes in a mechanical property during usage. Meta-materials thus permit designers to choose material components based on their static and/or dynamic performance. Designers may also tailor a meta-material based on its dynamic structure. This permits the freedom to choose suitable active or intrinsic materials and a suitable activation mechanism, such as one with low energy of actuation. Designing a meso-scale structure then includes material selection, activation element selection and design, and deformable structure (e.g., geometry and connectivity) design—weighed in both static and dynamic performance. This design flexibility permits a meta-material to vary over a wide range for controllable mechanical property of interest, such as stiffness.

In some designs, a mechanical property of a meta-material may change via: a) activation of one or more activation elements and their individual or combined effects on the mechanical property; b) acquisition of a different state for the deformable structure that changes the mechanical property, such as a new shape and resulting stiffness; and c) combinations of a) and b).

A meta-material as described herein may include any number of individual activation elements. From about 1 to about 1000 activation elements are suitable in many designs. More than 1000 activation elements may be used. Indeed, some meta-materials may include thousands of individually patterned activation elements on a compliant substrate. Some meta-materials may include from about 10 to about 100 activation elements.

The activation elements mechanically couple to the deformable structure. In general, coupling may refer to direct or indirect coupling, attachment, etc. Indirect coupling may include activation element attachment to an intermediate object or structure, which then attaches or otherwise couples to the deformable structure. Attachment may include chemical bonding such as adhesives, mechanical fastening, or any other suitable technique the prevents relative motion between two objects being attached. One of skill in the art is aware of different techniques to mechanically couple two objects and techniques suitable for specific materials. For example, a suitable adhesive will depend upon the two materials being joined, as one of skill in the art will appreciate.

External control may be flexibly achieved. Some embodiments employ electrical control, magnetic control, or other techniques according to the activation mechanism and operability of each activation element. Numerous examples will be described in further detail below. In one embodiment, mechanical connectivity of the deformable structure and activation elements is externally controlled in order to vary a mechanical property of the composite meta-material as a whole. The external control may use small amounts of energy to make large changes in the property of the structure. The present invention thus allows low-energy, small changes in component material shape, connectivity, or structure to produce larger changes in a mechanical property for the meta-material. Some embodiments of the present invention permit directional control of a mechanical property, such as stiffness. In many cases, the external control adds little mass or complexity, as exemplified by one or more common compliant electrodes (FIGS. 2G-2J).

Exemplary Meta-Materials

Figure 1A:
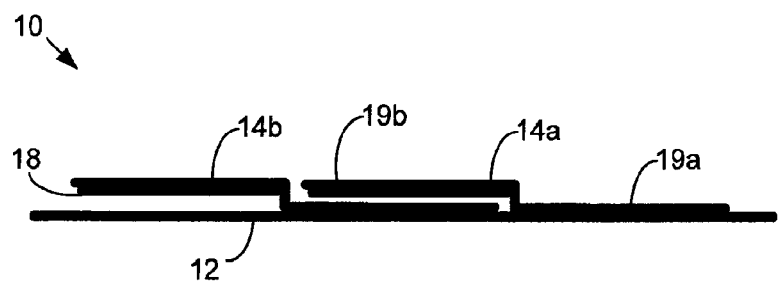
FIG. 1A illustrates a portion of a meta-material in accordance with one embodiment of the present invention.
Figure 1B:
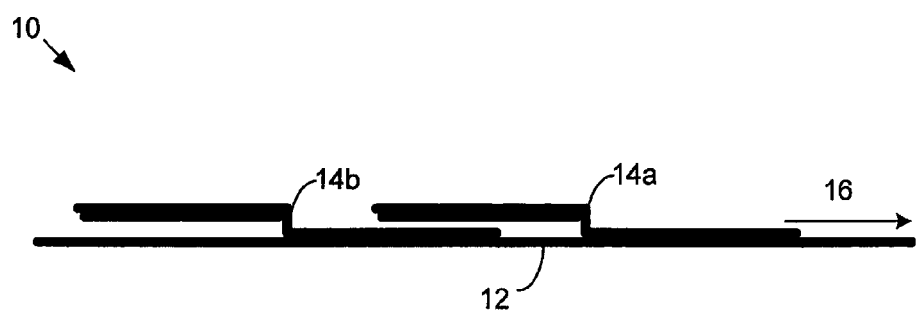
FIG. 1B illustrates the meta-material of FIG. 1A after being stretched in a lateral direction when activation elements included in the meta-material are de-activated.

FIG. 1A illustrates a portion of a meta-material 10 in accordance with one embodiment of the present invention. Meta-material 10 includes a deformable structure 12 and a set of activation elements 14. In this case, deformable structure 12 includes a compliant substrate. FIG. 1B illustrates the compliant substrate 12 and meta-material 10 being stretched in a lateral direction 16 when the activation elements 14 are de-activated. While meta-materials will now be described as objects, systems and components, those skilled in the art will recognize that the present invention also encompasses methods of performing actions related to these objects, systems and components.

Meta-material 10 includes a set of rigid activation elements 14 coupled to compliant substrate 12. Each activation element 14 comprises a rigid component 19 and an electrode 18. An attached portion 19a of rigid component 19 mechanically couples to the deformable structure 12. In this instance, portion 19a directly attaches to compliant substrate 12 using a suitable adhesive, for example. Other forms of direct and indirect coupling may also be used. An unbound, or 'free', portion 19b of each rigid component 19, which is not directly attached to compliant substrate 12, includes electrode 18 disposed thereon. In a specific embodiment, electrode 18 is disposed as a thin layer on a surface of a rigid component 19. For example, electrode 18 may include a metal sputtered layer disposed on a thin polyimide sheet 19. While only two activation elements 14 are shown for simplicity and understanding, meta-material 10 may include additional activation elements 14 in any planar direction on the top surface of deformable structure 12.

Activation element 14 includes two states: a) a de-activated state in which the free portion 19b is not coupled to another activation element 14, and b) an activated state in which the free portion 19b electrostatically (or by other activation means such as electromagnetic clamping) clamps to another activation element 14. In the electrostatic case, in order for clamping to occur, the voltages of each electrode 18 of each adjacent element 14 must be different. The meta-material in FIG. 1A may be extended in any direction and include more than two activation elements 14. In this case the voltages of any two adjacent activation elements must be different. This difference is normally achieved by having one element at an applied voltage and the other at a relative ground potential or voltage of opposite polarity.

Meta-material 10 thus employs electrostatic clamping as an activation mechanism. Electrostatic clamping adheres one material to another using an electric field across an insulator or dielectric material. In this case, the insulator includes the rigid component 19 of each activation element 14. An electrostatic clamping voltage is applied via electrode 18 and external control electronics (not shown) in electrical communication with electrode 18. The electrostatic clamping voltage temporarily fixes the free portion 19b of activation element 14a to the attached portion 19a of another activation element 14b that overlaps with the free portion 19b.

Thus, if there is no electrostatic clamping voltage on the activation elements 14, the free portions 19b for activation elements 14 can translate freely relative to each other and relative to the compliant substrate 12. This condition allows the compliant substrate 12—and meta-material 10—to bend or stretch according to mechanical properties of compliant substrate 12.

Once an electrostatic clamping voltage is applied, however, the activation elements 14 clamp to each other. This activation prevents relative motion between the two activation elements 14, and changes the mechanical properties of meta-material 10. For example, while the two activation elements 14 are electrostatically clamped together in the position shown in FIG. 1A, stiffness for meta-material 10 increases according to the stiffness of each rigid component 19. Mechanical properties other than the stiffness may change as well, such as the toughness, resilience, shear strength, etc, as will be described in further detail below. The bond between two rigid components 19 and activation elements 14 continues for as long as the electrostatic clamping voltage is applied up point where electrostatic attraction can no longer hold the stretching force. With suitable design, the clamping force (which is the resulting friction force due primarily to the electrostatic force exerted perpendicular to the surface) in this planar direction can be as great as the yield strength of the scale material.

The stiffness along direction 16 for meta-material 10 then varies from a minimum stiffness, when no activation elements 14 are activated and the meta-material 10 substantially assumes the mechanical properties of compliant substrate 12, to a maximum stiffness when all of the activation elements 14 are engaged by clamping to their adjacent partner. Thus, when no activation elements 14 are activated, meta-material 10 may be stretched in the lateral direction 16 as shown in FIG. 1B according to the compliance of substrate 12. Engaging activation elements 14, however, stiffens meta-material 10—and may lock the meta-material 10 into its current position depending on any external forces applied to the meta-material. The maximum stiffness for meta-material 10 will be the equal to the stiffness for the material used in each rigid component 19 provided that the pulling force 16 is not great enough to overcome the electrostatic clamping force between the overlapping activation elements 14.

Some meta-materials and activation mechanisms permit tunable control of a mechanical property. Consider damping. In this case, damping for meta-material 10 may vary between the minimum and maximum extremes. In general, each activation element 14 provides a controllable amount of frictional resistance (damping) to external deflection according to a) the strength of the applied electrostatic clamp, and b) the amount of surface area for the electrostatic clamp. Both these effects vary the friction between the two clamped elements. These elements slide with respect to each other when the material is stretched in the plane. This friction induces damping. Varying the electrostatic clamp voltage will alter strength of the electrostatic bond between two activation elements 14. In this manner, control electronics may be used to dynamically alter (e.g., during usage in response to closed loop control) the damping provided by meta-material 10 by increasing or decreasing the electrostatic clamp voltage provided to one or more activation elements 14. For example, the applied voltage may be reduced such that the damping provided by each activation element 14 reduces by one-half. Other voltage fractions and resultant strength levels may be used, as desired. In addition, the amount of surface area may also be dynamically varied to affect changes in damping for meta-material 10.

In one embodiment, meta-material 10 includes separable control for subsets of activation elements 14. In a specific embodiment, meta-material 10 comprises independent addressing and control for each activation element 14 in the meta-material 10. For embodiments where the meta-material 10 includes dozens or hundreds or thousands of individual activation elements 14, aggregate stiffness for the meta-material may then be tunably controlled by activating an appropriate number of activation elements 14 to achieve a desired stiffness. For example, if a number of elements are activated so that the total length of the clamped elements comprises half the total length of the compliant substrate 12 then the material will have twice the stiffness of the substrate alone in the direction along this measured length. The precision of tunable control will depend on the number of activation elements 14 and granularity of electrical addressing.

The minimum and maximum stiffness provided by meta-material 10 may be tailored before usage during design and fabrication, similar to the conventional design of composite materials. For example, elastic properties of each rigid component 19 may be selected during design, which will affect the maximum stiffness provided by meta-material 10. The surface area overlap between activation elements 14 may also be pre-determined for an application to provide a desired maximum strength at which stiffness may be controlled. In addition, compliant substrate 12 may be designed and selected to provide a desired minimum stiffness.

Meta-materials 10 and 20 illustrate simplified designs. Other designs are possible. For example, the electrostatic clamping can be of a non-planar topology. An example of this is a fiber or ribbon that fits inside of a tube. The fiber or ribbon and tube each have an electrode insulated by a dielectric insulating layer. When not activated the fibers or ribbons can slide inside of the tube. When activated, electrostatic clamping between the fiber or ribbon and the tube prevents sliding or allows sliding with additional damping (as desired). Alternatively each fiber or ribbon can contain a single conducting electrode that is completely covered by an insulator. In this case activation is produced by charging adjacent fibers with the opposite polarity so that the clamp to each other. These tubular structures may be arrayed on the surface or throughout the volume of a deformable or reconfigurable structure. They may be aligned in a single direction to control stiffness or damping in that direction only or they may be aligned in several directions. The fibers may run the length of the material or only partway through the material. Meta-materials may also include multiple embodiments described herein combined into a single structure. For example, stacking several of the meta-materials described in FIG. 1A could form a thicker meta-material. In this case, a spacer may be disposed between layers to ensure that the rigid components 14 are not forced against the compliant substrate 12. The spacer could be located at the attachment point of the activation element so as not to interfere with the motion of the activation elements. An example of such a meta-material composed of stacked layers is presented below in FIG. 8C.

If the meta-material is comprised of stacked layers then it is also possible to activate the layers differently so that the resulting mechanical properties is a combination of the stiffness or damping of each layer. For example, some layers may focus on controlling damping while others could focus on controlling stiffness. In another example, some of the layers could be made stiffer than the others so that the resulting stiffness is a combination of the stiffness of each layer. Note that each layer need not be of identical geometry or use identical materials. For example, some layers may be designed for providing damping control while other layers are better designed for stiffness control or providing a greater strength in the clamped state (such as by allowing a lot of overlap of activation elements). In another example, some of the layers may be more optimally designed to provide one range of stiffness while other layers are more optimally designed to provide another range of stiffness (such as by selecting the underlying deformable layer or the size and spatial density of the activation elements). Stiffness can then be controlled over a wide range but to a very fine degree by activating a combination of layers that are designed to function best over a specific range of stiffness.

Figure 1C:
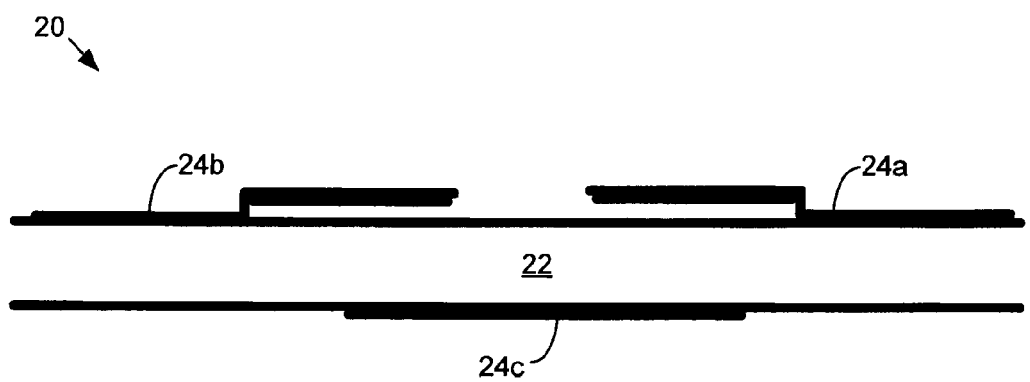
FIG. 1C illustrates a portion of a meta-material with rigid activation elements on both sides of a compliant layer in accordance with another embodiment of the present invention.

FIG. 1C illustrates a portion of a meta-material 20 in accordance with another embodiment of the present invention. Meta-material 20 includes a deformable structure 22 and a set of activation elements 24. In this case, deformable structure 22 includes a compliant layer whose thickness and elastic properties are selected to provide mechanical properties for the meta-material 20 when no activation elements 24 are activated. Activation elements 24*a* and 24*b* are disposed on a top surface of compliant layer 22, while activation element 24*c* is disposed on the opposite surface of compliant layer 22.

Similar to meta-material 10, meta-material 20 relies on electrostatic clamping as an activation mechanism and includes a set of rigid activation elements 24. Surface electrostatic clamping activation elements are also referred to herein as 'scales'. The scales include small (relative to the deformation and application of interest) rigid elements on the surface of a deformable structure that form a covering. The scales may include similar parts that collectively form a larger structure such as a controllable skin. In one embodiment, scales 24 are metal and double both as a rigid component and an electrode. Meta-material 20 may then be externally and electrically controlled to change between a compliant de-activated state and a rigid activated state. In the de-activated state, meta-material 20 substantially assumes the properties of compliant layer 22. In the activated state, the meta-material substantially assumes the properties of the rigid activation elements 14, as limited by the clamping strength.

Meta-material 20 mainly differs from meta-material 10 in that the rigid activation elements 24 are on opposite surfaces of the deformable structure 22. In this case, an electric field is established across the compliant layer 22, which doubly acts as a dielectric layer and deformable structure. When the clamping voltage is applied, the activation elements 14 form a continuous string of rigid material, even though the activation elements 14 are on opposite sides of the compliant layer 22 (they still vertically overlap to allow electrostatic clamping).

In a specific embodiment, an electrically controllable meta-material 20 employs electrostatic clamping of metallic rigid elements on an elastomeric compliant layer 22. In this case, each metallic element doubles as both the rigid element and electrode. When the metallic scales electrostatically clamp to the elastomer, meta-material 20 has a stiffness and strength similar to those of the metal. When the metallic scales are de-activated, the meta-material has stiffness resembling the stretchable elastomer. Intermediate strengths and stiffnesses can be achieved by varying the applied clamping voltage, or by altering the number of metallic scales that are electrostatically clamped, respectively.

Figure 3A:
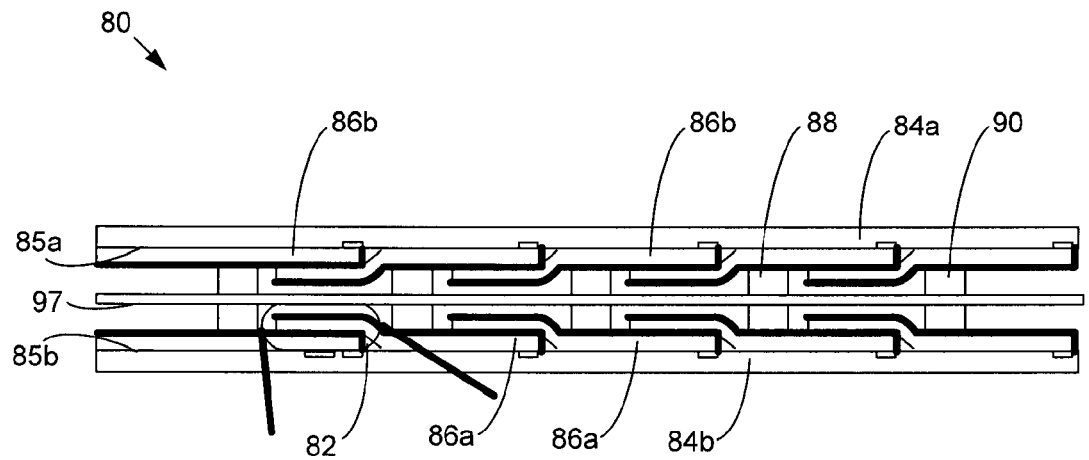
FIG. 3A illustrates a cross-section of a meta-material that provides the ability to control bending stiffness as well as planar stiffness in accordance with a specific embodiment of the present invention.

In another specific embodiment, each activation element 24 may include surface roughness or lips to enhance clamping strength. FIG. 3A shows an example of such activation elements suitable for use with many embodiments described herein. Lighter clamping also allows sliding of the activation elements 24 with friction as described above for the previous embodiment meta-material 10. This permits damping control using meta-material 20, as will be described in further detail below.

Figure 2A:
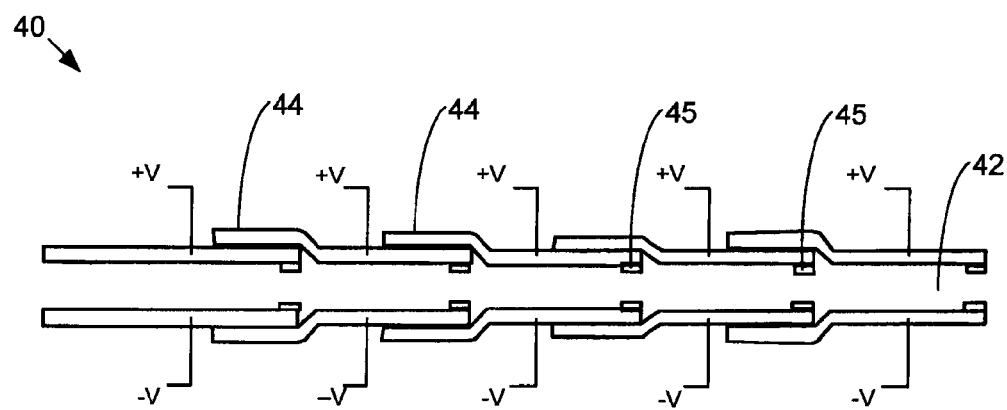
FIG. 2A illustrates a meta-material in accordance with a specific embodiment of the present invention.
Figure 2B:
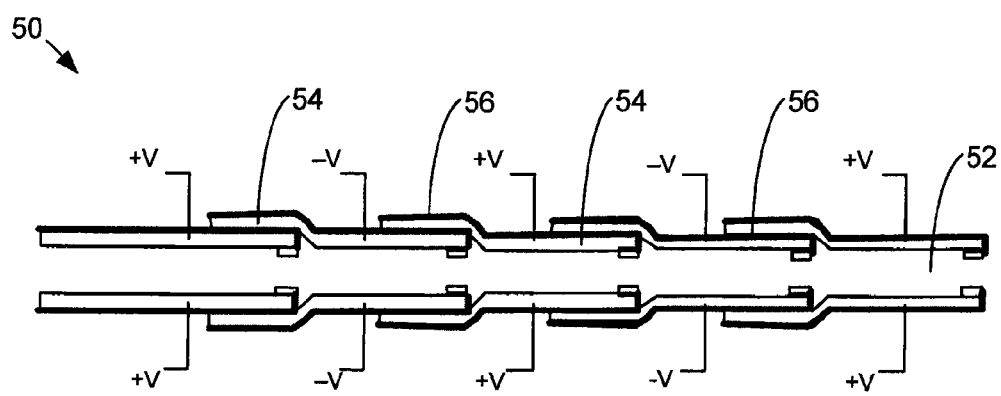
FIG. 2B illustrates a meta-material in accordance with another specific embodiment of the present invention.

FIG. 2A illustrates a meta-material 40 in accordance with a specific embodiment of the present invention. FIG. 2B illustrates a meta-material 50 in accordance with another specific embodiment of the present invention.

Each activation element 44 attaches to compliant layer 42 at an attachment point 45. Applying an electrostatic clamping voltage to each activation element 44 also causes a rigid portion of each element to adhere to an adjacent activation element 44. Collectively, when a clamping voltage is applied to all activation elements 44 in meta-material 40, the activation elements 44 form a continuous rigid layer that regulates mechanical properties of meta-material 40.

Referring now to FIG. 2B, each activation element 54 in meta-material 50 includes an insulating layer 56. The insulating layer 56 is disposed on a rigid component so as to rest between a) an electrode of one activation element 54 and b) another overlapping activation element 54 on the same surface of compliant layer 52. The insulating layer 56 enables electrostatic clamping between two overlapping activation elements 54. In this design, compliant layer 52 functions as a mechanical substrate only, while insulating layer 56 is used for electrostatic clamping between activation elements 54. The compliant layer 42 design of FIG. 2A is simpler from the perspective of the number of materials used, but the compliant layer 42 serves both electrical and mechanical roles, so material requirements for compliant layer 42 are more stringent.

Meta-material 40 of FIG. 2A operates similar to meta-material 20 described above in that an electric field is established across the compliant layer 42 to provide electrostatic clamping for active elements 44. For example, a positive voltage may be applied to each activation element 42 on the top surface while a negative voltage is applied to each activation element on the bottom surface. For the meta-material 50 of FIG. 2B however, adjacent active elements 54 on one surface of compliant layer 52 alternate polarity of the applied voltages to create a potential difference between overlapping activation elements 54 on that surface and across each insulating layer 56.

In another embodiment similar to that of FIG. 2A, the active elements consist of a rigid layer that also serves as an insulating layer with a conductive layer on top of this insulating layer that serves as an electrode. In a specific embodiment of this meta-material, the compliant layer is a silicone polymer such as Dow Corning HS IV (Dow Corning Corp., Midland, Mich.) that is from 0.01" to 0.05" thick. The insulating rigid layer is polyimide such as Kapton (DuPont Corporation, Route 23 South and DuPont Road, Circleville, Ohio 43113) from 0.00025" to 0.002" thick. The conductive layer is a metallization coating of gold that is deposited on top of the polyimide by sputtering or other means. An AC voltage from 500V to 4000V is applied across the scales. In another specific embodiment the conductive layer is carbon-impregnated silicone such as RTV 60-CON from Stockwell Rubber Co. (Philadelphia, Pa.) approximately 0.005" thick and the insulating layer is polyurethane 0.001" thick such as PT6100S from Deerfield Polyurethane Inc. (P.O. Box 186, South Deerfield, Mass. 01373). In this embodiment the rigid layer is Kapton polyimide that is 0.002" thick. The rigid layer is attached to the surface of the electrode opposite that of the insulating layer using the carbon-impregnated silicone electrode as an adhesive.

Figure 2C:
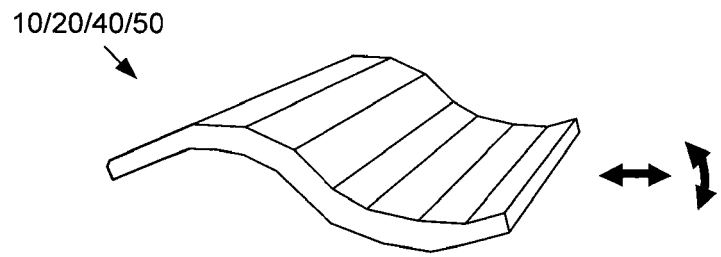
FIG. 2C illustrates the meta-material of FIG. 2A or FIG. 2B with an out of plane deformation.

Meta-materials 40 and 50 are each capable of planar and/or out of plane deformations. Planar deformations may include linear or planar elastic or plastic stretching, for example. Out of plane deformations may include bending, twisting, shearing, indenting, etc. Deformations may also include combinations of planar and out of plane deformations. FIG. 2C illustrates a perspective view of any of meta-materials 10, 20, 40 or 50 with out of plane deformations. When such a position has been achieved (e.g., using an electroactive polymer, see FIG. 2F), the activation elements may then be activated to lock the meta-material in its current position. As will be described in further detail below, this ability to position and reshape a meta-material while compliant and then lock in the meta-material in a desired position lends use of the meta-material to morphing and other variable stiffness or shape control applications.

Figure 2D:
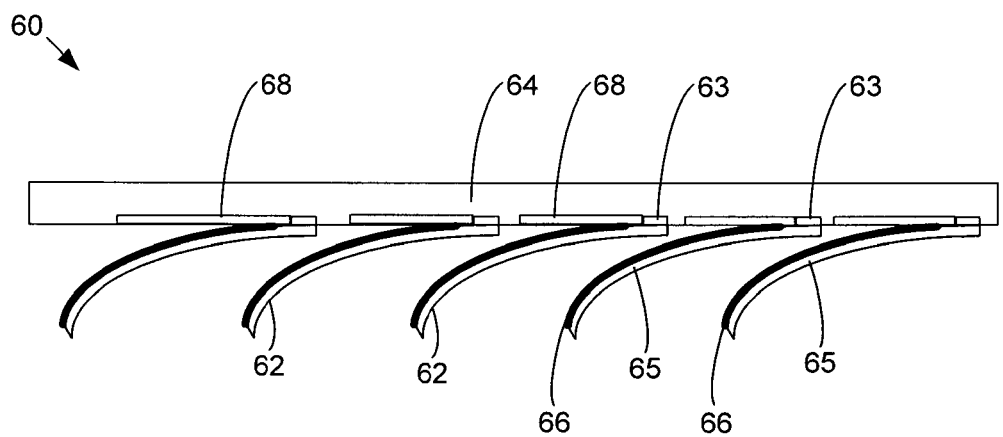
FIGS. 2D and 2E illustrate a meta-material including compliant electrodes and bendable but not extendable activation elements in accordance with another embodiment of the present invention.
Figure 2E:
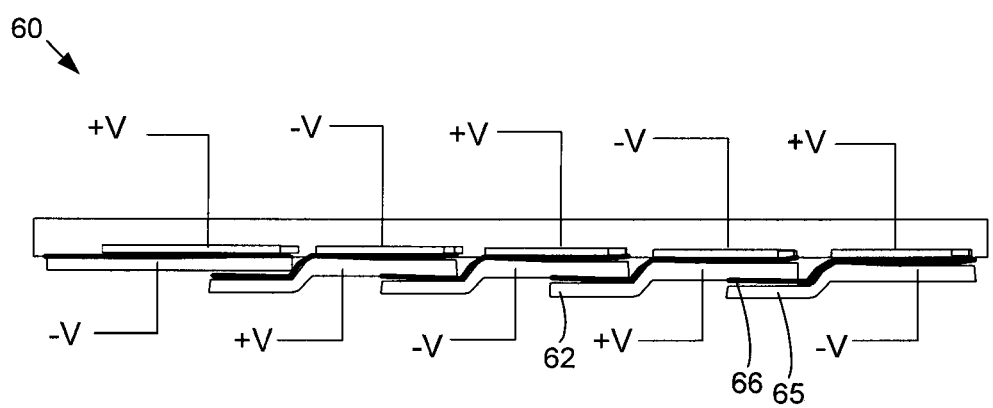

The present invention also contemplates other electrostatic clamping designs. FIGS. 2D and 2E illustrate a meta-material 60 in accordance with another embodiment of the present invention. Meta-material 60 includes activation elements 62 disposed on a single side of a deformable structure 64. In this case, deformable structure 64 includes a compliant layer with compliant electrodes 68 disposed thereon.

Each activation element 62 includes a non-extensible component 65 and an insulation layer 66. Non-extensible component 65 provides planar stiffness and also doubles as an addressable electrode for each activation element. Insulation layer 66 permits electrostatic clamping across its thickness. In an alternative embodiment, the insulation layer 66 may also be the non-extensible element 65 and the electrode could be a thin coating applied to the bottom surface of this element (away from the compliant layer). An attachment point 63 forms a connection between each activation element 62 and compliant substrate 64.

Figure 2F:
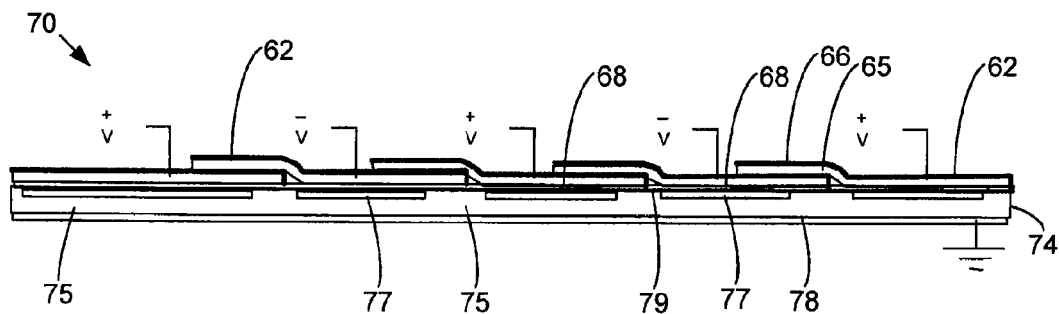
FIG. 2F illustrates a doubly controllable meta-material in accordance with one embodiment of the present invention.

Compliant electrodes 68 are disposed on the same side of compliant substrate 64 as activation elements 62. In one embodiment, compliant electrodes 68 are embedded within the surface of substrate 64. In another embodiment, compliant electrodes 68 comprise a thin coating applied in a selective area pattern to the surface of substrate 64 (FIG. 2F). For example, the compliant electrode may include a carbon-impregnated polymer patterned with a stencil. The compliant electrode 68 adds little stiffness to meta-material 60 and does not substantially affect de-activated expansion and contraction of compliant layer 64. In addition, the carbon-impregnated polymer adds little thickness to meta-material 60.

Each activation element 62 is bendable but not stretchable (non-extensible or non-extendable). For example, thin and bendable stiff component 65 may include a thin layer of aluminum (e.g. similar in thickness to aluminum foil), while insulation layer 66 includes a thin and bendable layer of polyimide. Collectively, the activation element 62 may bend (low bending modulus) in response to electrostatic clamping forces and a voltage difference between the metal electrode component 65 and electrode 68. After activation, each bendable element 62 then forms a surface topography corresponding to electrostatic clamping forces applied thereto.

Collectively, when all activation elements are clamped, meta-material 60 assumes a planar stiffness according to the non-stretchable stiffness of activation elements 62. Again, individual addressing between each activation element 62 and compliant electrode 68 permits granular and variable control of damping for meta-material 60. Thus, a lesser electrostatic clamping voltage may be applied to one or more of the activation elements 62. Stiffness may be controlled by selectively addressing only certain adjacent pairs of activation elements 62. Although not shown, it is understood that meta-material 60 may include activation elements 62 on both sides of the compliant substrate 64. In one embodiment, more than one layer of activation elements may be used to effectively control out-of-plane deformations. Multiple layers can be achieved by having activation elements on both sides of the deformable substrate or by stacking multiple layers of deformable substrates each with a single layer of activation elements (as described above).

Figure 8A:
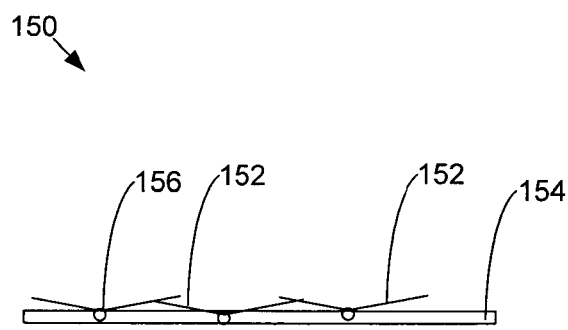
FIGS. 8A and 8B illustrates a meta-material with activation elements arranged over the surface so as to allow stiffness and damping control in response to any planar direction in accordance with another embodiment of the invention.
Figure 8B:
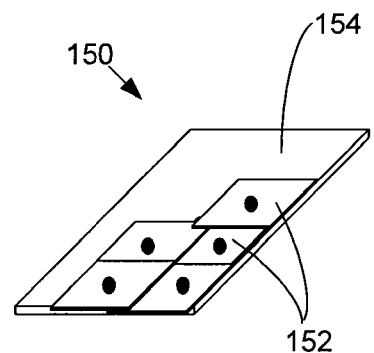

Thus far, the embodiments have shown overlap of activation elements in a regular pattern in a single direction. That is, the scales are arranged in rows. Such arrangements are well suited for materials where the external loads are applied in one direction (such as pulling on the ends of the material. A meta-material is not limited to such a simple arrangement and other arrangements are contemplated. FIGS. 8A and 8B show side and perspective views of a meta-material 150 having activation elements 152 that overlap over a substantially planar surface 154 so that there is overlap between elements 152 in all planar directions. Such an arrangement of scales 152 allows the material 150 to respond as desired to loads in all planar directions as well as bending moments applied to the material 150. These overlapping activation elements 152 can be disposed on one or both sides of the planar surface 154.

Such a meta-material 150 may be fabricated by many means know to those skilled in the art. It is possible to make overlapping scales 152 by taking advantage of the deformation of the deformable structure 154. For example, the deformable structure 154 can be first elongated in both planar directions. A flexible non-extendable layer is then deposited on top of this deformable layer and glued at the attachment points 156. This layer is then cut or etched into discrete scales 152 (such as squares or another suitable shape) using laser cutting or photolithographic means. The deformable layer 154 is now relaxed to a less extended state causing the scales 152 to overlap in all directions.

Figure 8C:
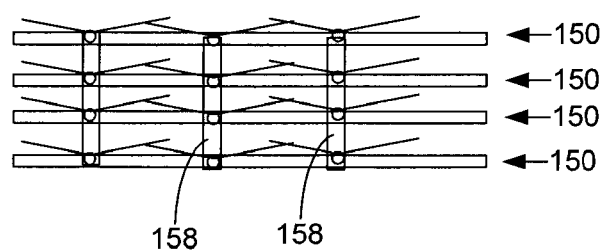
FIG. 8C illustrates a meta-material comprised of several stacked layers of component meta-materials so as to allow for greater thickness and control over forces and moments in any direction in accordance with another embodiment of the invention.

Several layers of meta-material 150 can be stacked to form a multilayer meta-material. FIG. 8C shows one example of how such layers may be stacked. As discussed above, adjacent meta-material 150 layers may be inter-connected with spacers 158 located at one or more attachment points of individual activation elements 152.

Figure 2G:
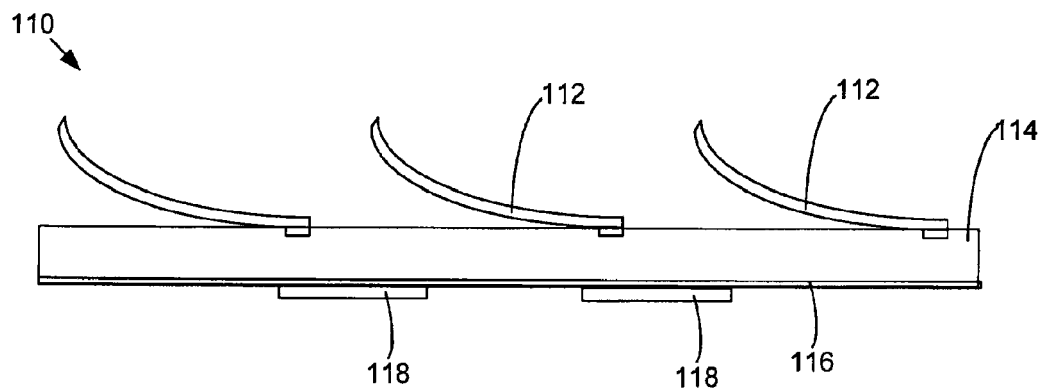
FIGS. 2G and 2H illustrate a meta-material with a common electrode in accordance with another embodiment of the present invention.
Figure 2H:
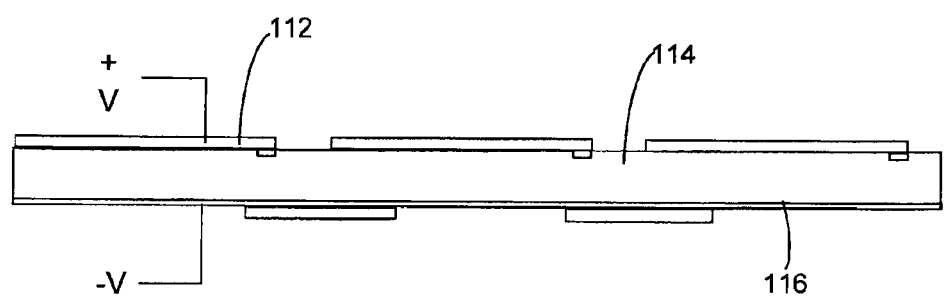

FIGS. 2G and 2H illustrate a meta-material 110 in accordance with another embodiment of the present invention. Meta-material 110 includes activation elements 112, compliant substrate 114, electrode 116, and rigid elements 118.

Activation elements 112 are bendable but not substantially extendable. For example, elements 112 may include a thin and bendable layer of metal (e.g., similar to tin foil thickness or another thickness so long as the layer is bendably responsive to electrostatic clamping forces) or another non-conductive material (e.g., polyimide). Activation of elements 112 beings them into contact with the top surface of compliant substrate 114. At this point, planar stiffness of the material controls planar deflection of each activation element. As with any stiff or rigid material, a large enough force will lead to minor elastic deflection, but non-extendable herein refers to the concept that the material is stiff enough to resist deflection for forces expected to be witnessed by meta-material 110.

Compliant electrode 116 services electrostatic clamping for each activation element 112. For example, a voltage may be applied via common electrode 116 to simultaneously trigger each activation element 112. Alternatively, compliant electrode 116 may be used as ground where activation element 112 is individually addressed via an electrode included therein (e.g., a conductive activation element or an electrode patterned on a non-conductive activation material) to apply an electrostatic clamping voltage. In either case, compliant substrate 114 acts as an insulation layer between electrode 116 and each activation element 112.

Electrostatic clamping across compliant substrate 114 draws each bendable activation element 112 to the top surface of compliant substrate 114 and connects overlapping (non-extendable) activation elements 112 and rigid elements 118. Cumulatively, meta-material 110 activates to form a stiff planar material—with fewer activation elements 112 than meta-material designs presented so far. This reduces complexity of meta-material 110, and provides activation elements 112 that do not necessarily need to overlap with other activation elements 112.

Figure 2I:
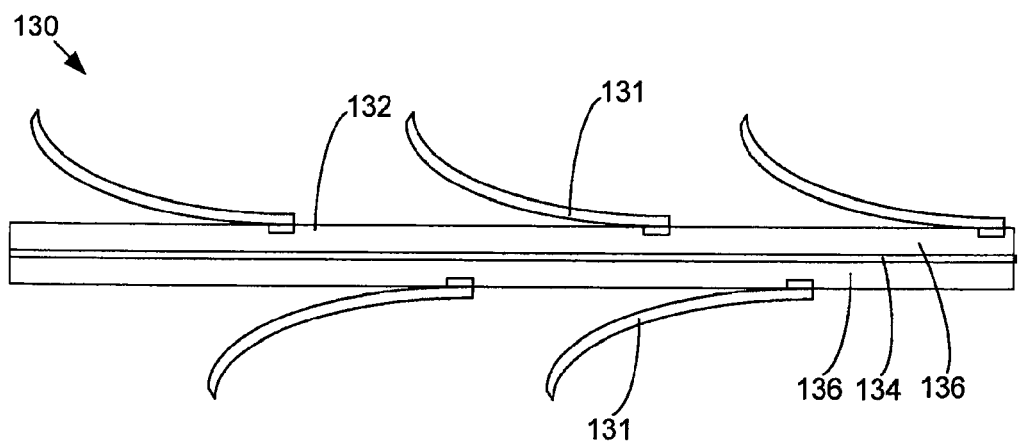
FIGS. 2I and 2J illustrate a meta-material including two compliant layers that on opposite sides of a compliant electrode in accordance with another embodiment of the present invention.
Figure 2J:
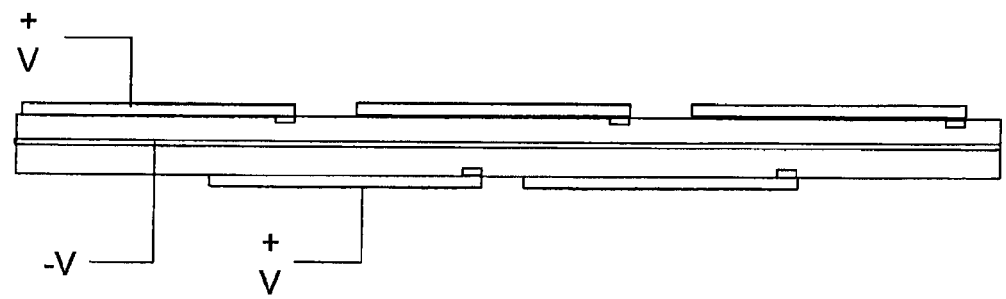

FIGS. 2I and 2J illustrate a meta-material 130 in accordance with another embodiment of the present invention. Meta-material 130 includes bendable but not extendable activation elements 131 and a layered deformable structure 132.

Deformable structure 132 includes a buried compliant electrode 134 disposed between two compliant layers 136. In this case, electrode 134 services both bottom and top layers of activation elements 131 through each respective compliant layer 136.

The absolute and relative size of each activation element is a design parameter and may vary. In one embodiment, electrostatic clamping activation elements are sized relative to the spacing between elements to ensure that there is surface area sufficient overlap between activation elements to allow electrostatic clamping, even when the compliant layer undergoes maximum strain. Activation elements with smaller absolute size allow for more intricate variations in strain for a meta-material. In one embodiment, if the activation elements are short, then thickness of each activation element is decreased to allow for bending during clamping and unclamping.

Width and orientation of scale-type activation elements on a planar compliant layer may also be varied. In one embodiment that supports expansion in both planar directions as well as shear strains, the activation elements are implemented with an aspect ratio (length vs. width) that is relatively low. An aspect ratio between about 1 and about 5 is suitable in many embodiments. To maintain multi-dimensional planar control of a mechanical property, the activation elements may overlap in both planar directions. Other aspect ratios may be employed. In another embodiment, narrow activation elements (a high aspect ratio) are employed. An aspect ratio greater than about 5 is suitable in many embodiments. The thickness of the scales is typically much less than the length or width. In one embodiment thickness is from 10 micrometers to 1000 micrometers.

When electrostatic clamping is sufficient to prevent sliding between individual activation elements, the stiffness and strength of the meta-material will not substantially depend on orientation of the elements, provided that there is sufficient overlap or voltage-induced electrostatic clamping in the clamped area to prevent sliding. The present invention, however, is not limited to any particular orientation, layout or distribution of activation elements on a deformable structure. In one embodiment, the activation elements are aligned in perpendicular and parallel rows and columns Distribution of the activation elements need not be so regular. In another embodiment, the activation elements form a radial, fanning, or another non-symmetric surface arrangement. Scales on fish and feathers on birds are two natural analogues that do not include perfectly regular organization of active elements on a deformable structure.

In some cases, Poisson contraction of a relatively thin compliant layer in a direction orthogonal to a large stretch may affect activation elements disposed on a surface of the compliant layer. To prevent such orthogonal contraction issues, meta-materials including a compliant layer may also include mechanisms for preventing bending, buckling or collapse of activation elements in the contraction direction. For example, the compliant layer may include one or more slits or recesses on a surface in the direction of stretch. When the material is strained, the slits open wider. While locally, Poisson contraction has not changed, the total amount of deformation in the transverse direction is reduced at the edges of the layer. This reduction in transverse motion helps prevent buckling and also ensures that a maximum amount of overlap is maintained in the active elements.

Other deformable structures and compliant layers can be used that inherently have less of a Poisson's contraction effect. These include compliant foams, including so-called Zero-Poisson's or auxetic foams.

Although the present invention has so far been described with respect to a few relatively simple meta-material designs, the present invention encompasses a wide variety of designs, shapes and structures that enable dynamic control of one or more mechanical properties. Indeed, the relative simplicity of many meta-material designs allows extension to countless other and more complex design alternatives. For example, the embodiments described so far have focused on skins that are flat. The invention is not limited to such flat topologies.

FIGS. 2K and 2L illustrates a meta-material 200 disposed in a cylindrical topology to vary the stiffness of a tube 202 in accordance with one embodiment of the present invention. Tube 202 may represent a fiber, rod, or another cylindrical surface or object. In one embodiment, the meta-material 200 is configured as a 'skin' about the outside cylindrical surface of a rod. In another embodiment, the deformable structure forms the main material of the rod with the activation elements functioning as a skin.

Meta-material 200 includes thin, bendable but not extendable activation elements 206. Clamping the activation elements 206 radially constricts their dimensions, and changes mechanical properties of meta-material 200. This confers variable stiffness and damping properties to meta-material 200.

Meta-material 200 demonstrates one example of how the present invention may be shaped (a cylinder). Meta-materials described herein may also conform to an arbitrary and complex surface shapes so long as the size of the activation elements is smaller (typically much smaller) than the size of the surface features.

Meta-material 200 also presents a relatively simple deformable structure (a tube or a substantially linear rod). More complex deformable structures are possible. In one embodiment, meta-material 200 forms a coiled spring. In this case, the present invention permits dynamic control of mechanical properties of the spring.

Figure 11A:
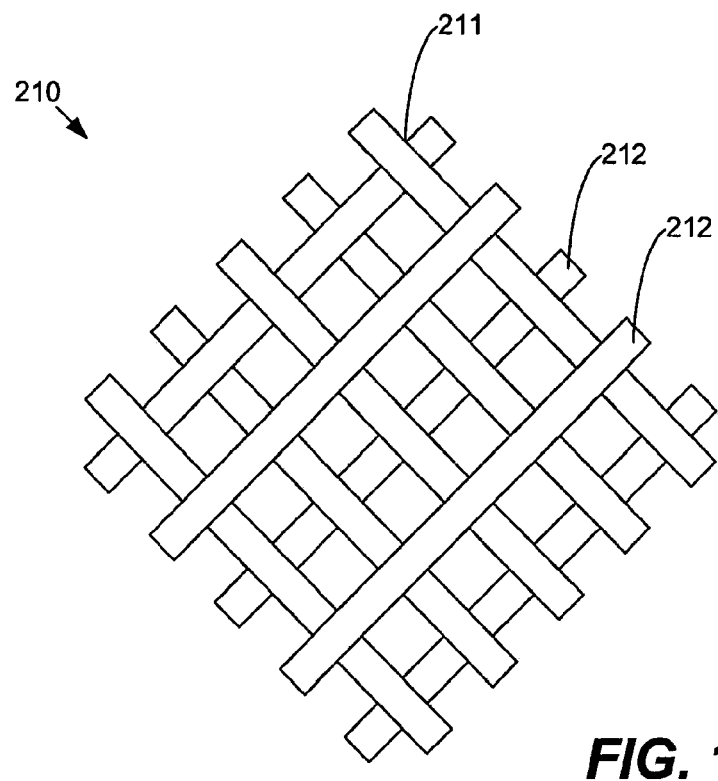
FIG. 11A illustrates a simplified view of a meta-material weave in accordance with one embodiment of the present invention.
Figure 11B:
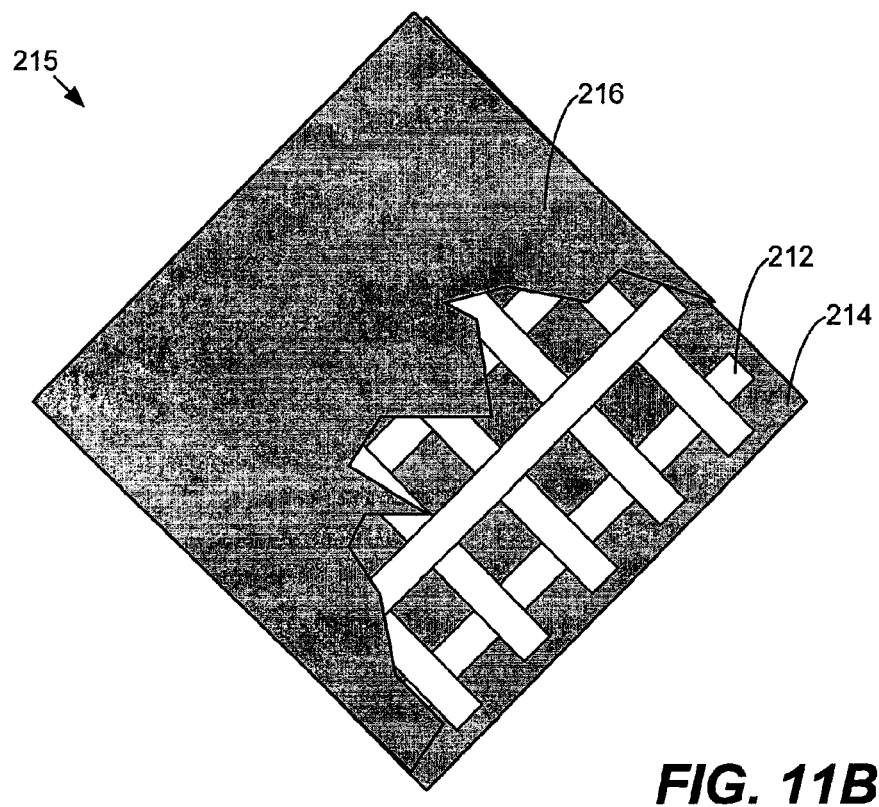
FIG. 11B illustrates a simplified view of a meta-material weave that can be rigidized by clamping it between two more rigid layers in accordance with another embodiment of the present invention.

In another embodiment, tube 202 acts as a fibrous material and is assembled into a weave or a similar macro-structure. FIGS. 11A-11B illustrate a simplified view of a meta-material weave 210 in accordance with two embodiments of the present invention. Meta-material weave 210 includes a woven deformable structure 211 and fibers (such as 200) or ribbons 212. This weave 210 may be formed into a cylindrical shape (e.g., laid over a cylindrical body) or may also be used in a planar form or in any surface shape much like the planar embodiments discussed previously. In this case, each ribbon 212 forms a planar activation element.

Each fiber 212 or ribbon 212 in the weave may be independently controlled to affect the overall performance of weave 210. In one embodiment, fibers 212 include electrostatic clamping activation elements, which when activated, prevent fiber 212 movement including the activation elements and reduce inter-fiber 212 movement. This effectively stiffens the weave 210. This clamping may be accomplished in several ways. Each fiber or ribbon 212 may include a conductive layer (electrode) trapped between insulating layers. If the electrodes in the fibers or ribbons 212 in each direction of the weave are charged to different voltages then electrostatic clamping between these fibers or ribbons will occur at the points where they cross over each other. In usage, some inter-fiber 212 sliding may be permitted to provide damping. Such a weave 210 with dynamically variable mechanical properties would find use in ballistics and other high-energy impact applications, for example. In these applications, the ability to dynamically tailor strain to failure and elastic modulus drastically increases the amount of energy that may be absorbed by the weave, as will be described in further detail below.

The meta-material 215 in FIG. 11B does not rely on ribbon-to-ribbon clamping but rather uses two flexible but non-extendable layers 214 and 216 located on each side of the woven layer 210. Each of these flexible layers 214 and 216 includes an electrode on its outer surface. When a voltage is applied across the two electrodes, the two layers 214 and 216 clamp together electrostatically and the woven layer 210 becomes trapped between the two flexible layers 214 and 216 and thereby prevented form deforming In another variation, the ribbons 212 of the woven layer 210 contain electrodes that are attracted to any one of the electroded outer layers when activated thereby restricting motion of the woven layer.

So far, the deformable structure has been relatively passive, but as noted above, the deformable structure can also be an active material. FIG. 2F illustrates a doubly controllable meta-material 70 in accordance with another embodiment of the present invention. Meta-material 70 includes two active components: electrostatically clamping activation elements 62 and an electroactive polymer actuator 74 that serves as a deformable structure.

Activation elements 62 include an insulation layer 66 and a thin and bendable stiff component 65. Activation elements are attached to the surface of electroactive polymer 75 at one end. Each activation elements 62 couples to the electroactive polymer actuator 74 and operates similar to that described above with respect to meta-material 60. Electrodes 68, which are disposed on a top surface of electroactive polymer actuator 74, service electrostatic clamping with activation elements 62.

Electroactive polymer actuator 74 includes a compliant electroactive polymer 75, such as a dielectric elastomer. Multiple compliant electrodes 77 are disposed on a first surface of electroactive polymer 75, while a single common compliant electrode 78 is disposed on the opposite surface of electroactive polymer 75. An insulation layer 79 is disposed between compliant electrodes 77 that service electroactive polymer actuator 74 and electrodes 68.

Actuation using one or more of electrodes 77 and electrodes 78 causes planar or linear expansion of electroactive polymer 75 (and a minor decrease in thickness). Electroactive polymer transducers may be configured in a wide variety of shapes and designs that affect resultant mechanical deformation in response to electrical input. For example, electroactive polymer actuators may be configured into sheets, rolls, and customized shapes to achieve a desired deflection. Stiffening members and actuator frames may also be used to customize mechanical output. Individual sheets may be stacked to form multiple layers. Several different electrode patterns may be made on the surface of a single sheet in order to allow for more complex shape changes. Further description of actuation of electroactive polymer actuators and devices is described in commonly owned U.S. Pat. No. 6,781,284, which is incorporated by reference herein in its entirety for all purposes. Further description of multiple electrode monolithic polymers is described in commonly owned U.S. Pat. No. 6,664,718, which is also incorporated by reference herein for all purposes.

Collectively, electroactive polymer transducer allows external control of the shape, deformation and size of meta-material 70. Once a particular shape or position has been acquired using electroactive polymer actuator 74, activation elements 72 may then be triggered to lock in a current position of meta-material 70.

Figure 3B:
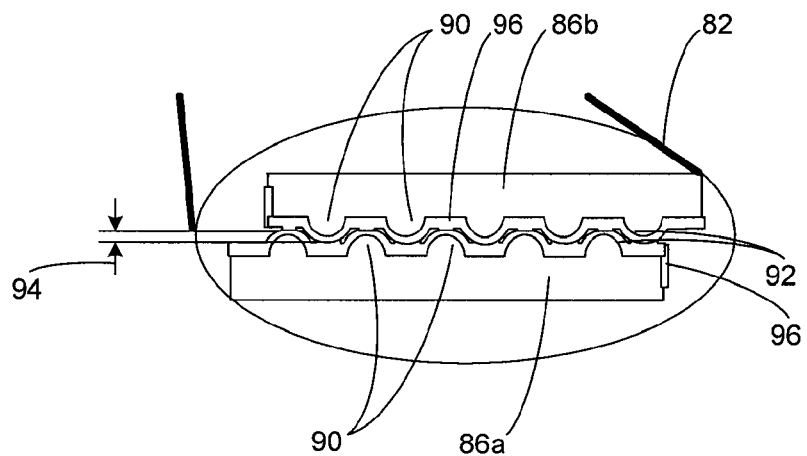
FIG. 3B illustrates an expanded portion of the meta-material of FIG. 3A that permits mechanical clamping.

FIG. 3A illustrates a cross-section of a meta-material 80 that provides the ability to maintain a locked or maximally stiff state with little or no external activation applied. Meta-material 80 comprises deformable structure 84, activation elements 86, spacer 88, and interlocking features 90 (FIG. 3B).

Deformable structure 84 includes two compliant layers 84a and 84b and two opposing surfaces 85: a lower surface 85a on a first compliant layer 84a and upper surface 85b on a second compliant layer 84b. A first subset of activation elements 86a is disposed on lower surface 85a, while a second subset of activation elements 86b is disposed on upper surface 85b.

Spacer 88 comprises a high stiffness material (compared to the compliant layers), couples to lower surface 85a of layer 84a, and couples to upper surface 85b on layer 84b. Spacer 88 may attach to each surface using an adhesive, for example. Functionally, spacer 88 separates the two surfaces 85 and provides a cavity that allows activation elements 86 to be located on inner surfaces of deformable structure 84. Spacer 88 need not be completely rigid and may even include a flexible foam. When subsets of activation elements on each layer 84 are clamped, the upper and lower layers 84 and their connected activation elements 86 each form a high planar stiffness, and spacer 88 separates the high stiffness layers. This separation increases bending stiffness for meta-material 80. Adjusting the geometry and length of spacer 88 enables the maximum bending stiffness to be adjusted substantially independently of planar stiffness. By controlling the stiffness of each set of activation elements, the bending stiffness can be controlled.

Meta-material 80 also employs a mechanical locking as an activation mechanism to maintain a particular position. FIG. 3B illustrates an expanded portion 82 of meta-material 80 in accordance with a specific embodiment.

Each activation element 86 includes interlocking features 90 that interact with interlocking features 90 on an overlapping activation element 86. The interaction is such that lateral and relative motion between two adjacent or overlapping activation elements 86 must overcome the current stiffness of meta-material 80. In this case, an interlocking depth 94 between mating features 90 on each activation element 86 must be vertically overcome before lateral motion between activation elements 86a and 86b may occur.

In this case, interlocking features 90 include parallel bulges 92 aligned in a planar direction orthogonal to displacement of the activation elements 86. The present invention may use other geometries to achieve mechanical locking. For example, the bulges may be squared at their distal ends or include other geometries. In addition, individual features may not be parallel and linear (into the page), and may include waves or other planar configurations that provide forces in two planar dimensions. This provides planar stiffness in multiple directions for meta-material 80 when the mechanical features 90 are locked.

Meta-material 80 thus uses interlocking features 90 to enhance locking at a particular position. In a specific embodiment, this design includes sufficiently stiff layers 84 such that meta-material 80 locks in a desired position with no electrical input or electrostatic clamping. This voltage-off locking reduces power consumption and allows meta-material 80 to have a more desirable fail-safe mode.

Alternatively, a small voltage difference (+/−V) is applied across electrodes 96 to help keep meta-material 80 more securely locked. To unlock meta-material 80, V is turned off and a second voltage, V2, may be applied to a central elastomeric layer 97. This voltage, V2, is greater in magnitude than V, and consequently attracts the free ends of the scales. This attraction breaks the contact between the overlapping scales and allows the outer elastic substrates to strain freely. V2 may be oscillated to help break contact between overlapping scales.

In other embodiments that employ electrostatic clamping, one of the dielectric insulators of each clampable pair of electrode and insulator activation elements, such as the flexible scales of FIGS. 2A through 2J, is replaced by a thin sheet of a material that maintains a permanent electrostatic charge. Such materials include vinyl and other polymers and are commercially available and used for a variety of applications such as temporary and reusable signage. In this case the sheet clamps when no voltage is applied to the complementary electrode and insulator element. The elements release or reduce clamping when a voltage is applied to across the two electrodes that creates an electric field that cancels that of the permanently charged sheets. Materials with permanent charge are well known. With this embodiment it is possible to maintain a maximally rigid state or fixed position with substantially no electrical energy input.

Meta-material 80 shows how a variety of features may be incorporated into a basic compliant layer meta-material design. Many other design enhancements are possible. For example, additional clamping layers may further increase the strength of a meta-material for a given voltage. The basic structure of 80 could be stacked to produce a thicker material that is capable of changing its planar and bending stiffness. It may be desirable to have activation elements for each of the layers arranged at different angles, to further ensure stiffness uniformity of the meta-material.

Other interlocking or latching techniques may be used to maintain the position for a meta-material. In one embodiment, mechanical latching is used to mechanically prevent to activation elements from separating. For example, one rigid activation element may include a male latch that mates with a female latch on a second rigid activation element. The coupled mechanical latch then resists any external forces that attempt to move the activation elements relative to each other. Activation may then include any suitable activation mechanism that moves the mating latches on their respective activation elements from a latched state to an unlatched state.

Material selection for activation elements and deformable structure in a meta-material will significantly determine overall mechanical properties of the meta-material. In general, material selection for a deformable structure, active elements and their components will vary with design of the meta-material. These materials may be chosen during design for suitability in an application, as one of skill in the art will appreciate. Performance-related factors that affect the choice of materials include the mechanical properties of strength, maximum elongation, stiffness, creep, tear resistance, tribology (friction and wear) and fatigue, surface roughness and electrical properties of dielectric strength and resistance. In some applications, smooth surfaces contacting each other may enable higher clamping forces by permitting more intimate contact between the surfaces. In other applications, a rough surface may be desired to permit mechanical interlocking as described above. Other performance-related factors may be relevant in certain applications and used to select component materials. Additional factors that will influence the selection of materials include temperature range of operation, moisture absorption, heat transfer, and electromagnetic signature. For example, materials may be selected to provide a desired environmental tolerance, a desired heat conduction and/or electromagnetic signature. Composite or plastic rigid activation elements with a weakly conductive coating can be used in place of metal to vary heat conduction and electromagnetic signature. Materials may also be selected to provide a certain stiffness or density. Alternatively, materials may be selected for their fabrication complexity or cost.

For the 'scale' type meta-material designs described above, the rigid component in each active element may comprise any material with a stiffness greater than the stiffness of the deformable structure. Exemplary materials include rigid polymers, rigid plastic plates with sprayed conductive rubber, ceramic plates and papers (felts) or other layers made out of ceramic fibers, ceramic foams, metal foams, carbon-fiber composites, metals and rigid metal plates, such as aluminum, rigid plastic electrodes with thin laminated metal coatings, flexible electrodes including various types of conductive fabric, and carbon laminates (which are used as a skin on aircraft, for example). Other materials may be used. The rigid components may also include a non-conductive and high stiffness material that is coated with a conductive coating.

Conductive coatings or layers may include any suitable electrical carrier, such as a carbon impregnated polymers, metallic spray or sputtered coating, or any other suitable conductor available to one of skill in the art. Because electrostatic forces typically operate at high voltage and low current, the conductive layer need not be very conductive. In fact, the natural conductivity of carbon fibers or other carbon particles, even diminished by mixing them into a non-conducting polymer matrix, is more than sufficient in many cases.

Materials used for the deformable structure will depend on a particular design. Thin compliant layers not relied on for electrical performance may include any material having a suitable compliance. Exemplary materials include rubber, compliant polymers, silicone rubber, many rubbers such as natural latex rubber, nitrile rubber, polymer foams (including the aforementioned zero-Poisson's and auxetic foams), patterned flexible but non-extendable polymers so that local areas can flex instead of stretch, arrays of metal or polymer springs, metal meshes, and stretchable fabrics such as those made by including elastic fibers. For example, by making numerous slits in the polymer in a direction transverse to the direction of compliance. The slits may be arranged in a "brick-like" pattern such that adjacent rows of slits in the transverse direction are offset so that the slits do not align in the compliant direction. Another example is to form the polymer into a honeycomb structure, such as that of structure 102 of FIG. 4A, where the polymer is able to flex by bending at the vertices. Another example is to form the polymer sheet into a structure that deforms in the out-of-plane direction such as a sheet with transverse folds that allow it to accordion, patterned metal sheets (that function like the polymers An elastomeric substrate that doubly provides electrical and mechanical performance can be selected from a variety of materials. Exemplary materials include, acrylic elastomer, silicone rubber, nitrile rubber, PolyVinlyleneDiFlouride (PVDF), and polyurethane elastomer, for example. Silicone rubber provides good environmental tolerance, large strain capability, and good insulation (for the compliant layer insulated versions).

The scale-insulated embodiments may use a polymer coating with good insulation properties and environmental tolerance, such as silicone rubber or polyimide. If metallic scales or coatings are used, the insulating layer may also include a non-conducting metal oxide (e.g., anodized aluminum) that is formed directly on the metal.

In embodiments that use a conductive deformable structure and clamping resulting from scales being attracted to electrodes on the surface of the deformable structure, separate electrodes on the deformable structure are not required.

In a specific embodiment, a meta-material measuring about 6 in2 includes a silicone rubber compliant substrate layer with thin steel scales for rigid activation elements. An electrode on one side of the elastomer included a coating of carbon particles in a silicone binder. In this specific embodiment, the electrode is compliant.

Although meta-materials have so far been described with respect to relatively simple planar deformable structures, it is understood that deformable structures may include thin-layered complex shapes, bodies with complex surfaces, and structures with multiple components. As noted above, for example, individual layers may be stacked or formed into cylinders. In addition, meta-materials so far have been discussed primarily with respect to electrostatic clamping and electroactive polymers for activation mechanisms. A meta-material may use other activation mechanisms.

Figure 4A:
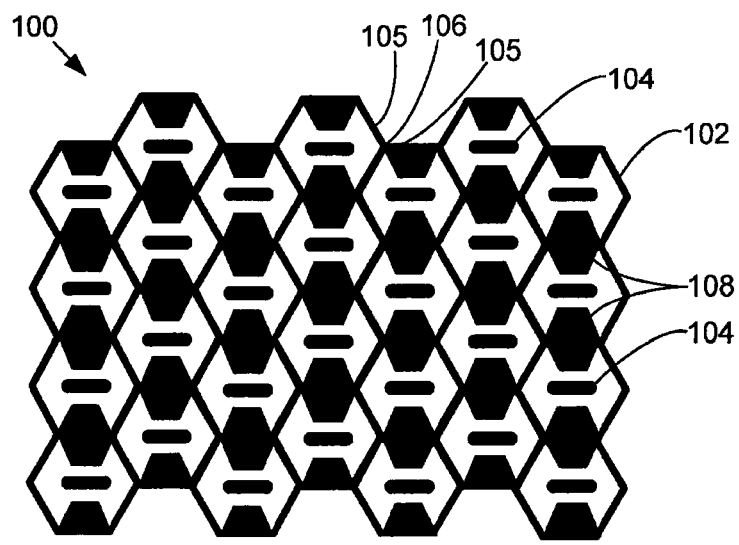
FIG. 4A illustrates a meta-material including magnetic activation elements in accordance with another embodiment of the present invention.
Figure 4B:
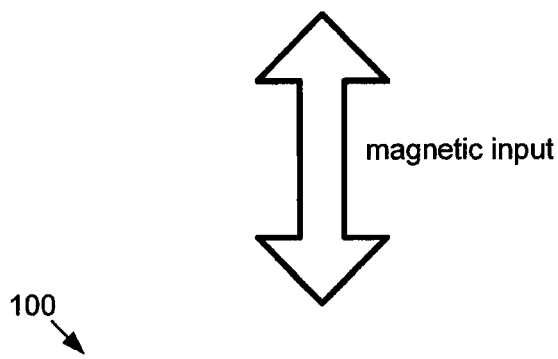
FIG. 4B illustrates the meta-material of FIG. 4A after activation of all elements in the meta-material.
Figure 4B:
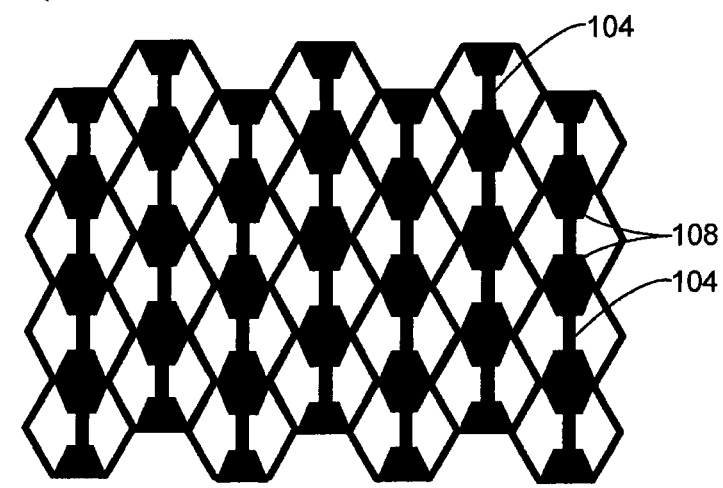

FIG. 4A illustrates a meta-material 100 that uses a magnetic activation mechanism in accordance with another embodiment of the present invention. Meta-material 100 comprises a honeycomb deformable structure 102 and magnetic activation elements 104. FIG. 4B illustrates meta-material 100 after activation of magnetic elements 104. Meta-material 100 differs from previous embodiments in that it includes multiple rigid elements and a deformable structure that reconfigures in shape as opposed to stretching.

Deformable structure 102 comprises a honeycomb lattice with relatively rigid members 105 and flexible joints 106. Each joint 106 pivotally couples two or three rigid members 105. In the activation state shown in FIG. 4A, deformable structure 102 may be compressed and expanded, e.g., like an accordion. Such structures can be made by a variety of known techniques including the extrusion of polymers, metals or polymer-fiber composites, for example.

Activation elements 104 may be controlled to assume two states: a) a first position or orientation (FIG. 4A) in which each activation element 104 does not substantially interfere with deformation of honeycomb lattice 102 or otherwise contribute to the stiffness (or another mechanical property) of meta-material 100; and b) a second position or orientation (FIG. 4B) in which each activation element 104 increases the stiffness (or another mechanical property) of meta-material 100. In the second position, a stiff component of each activation element 106 interfaces with rigid blocks 108 in each honeycomb of deformable structure 102. This prevents vertical displacement or relative motion between vertically adjacent rigid blocks 108 above and below an activation element 106. When multiple activation elements 106 have been activated, this cumulatively prevents movement of rigid members 105 and joints 106 in the honeycomb lattice that neighbor the activated elements 106. Activating all activation elements 106 in meta-material 100 immobilizes the entire deformable structure 102 in the position shown in FIG. 4B.

In one embodiment, activation elements 104 respond to magnetic input and can rotate about an axis into the page of FIG. 4A (e.g. they are supported at either end by a pivot or in the center by a rotary joint). The orientation of a magnetic field (such as by electrically controllable coils external to meta-material 100 or embedded in certain layers of the composite) determines the direction of the magnetic activation elements 104 and therefore the stiffness of meta-material 100.

Other designs may deliver a magnetic field across individual elements 104 to control activation into either position state. A permanent magnet or array of magnets may be repositioned outside of the meta-material in order to control its properties.

Meta-material 100 provides another example where interaction between deformable structure 102 and magnetic activation elements 104 allows a small change in energy applied to change the state of activation elements 104 to affect a large change in an overall property for meta-material 100. At the least, the change in state for activation elements 104 changes the overall stiffness for meta-material 100.

The magnetic input may also have each activation elements 104 assume an intermediate position between the two states. This may be advantageous, for example, to acquire an intermediate aggregate effect for the meta-material 100 such as a lesser stiffness in between the two extremes. Intermediate stiffness states may also be achieved by rotating the active element of only some of the individual cells. For example, if only every other row is made rigid then the total rigidity is far less than if every element is aligned for maximum rigidity. Permanent magnets may also be used to make the structure function in reverse. In this case, the activation includes an electromagnet located in the vicinity of the permanent magnet that cancels the magnetic attachment of the permanent magnet and causes normally magnetically clamped elements to come unclamped and thus result in a change of connectivity and resulting stiffness.

In a specific embodiment, deformable structure 102 includes a plastic or metal material. Other materials may be used. The flexible joints 106 may include live hinges, thinned corners for plastic, interlocked pieces with slits (common in the paper industry), or any other mechanism that allows deformable structure 102 to change shape. Activation elements 104 may include a ferromagnetic material, coil, or a permanent magnet, for example. A component may also be included to house the ferromagnetic material, such as a plastic piece that provides structural strength. Element 104 may also include a paramagnetic material or other material that will preferentially align itself in a magnetic field gradient.

Although the deformable structure 100 has been described primarily with respect to magnetic manipulation of activation elements 104, other techniques may be used to control the activation elements. In another embodiment, activation elements 104 respond to electrical input to change position. In this case, an actuator responds to an electrical signal and mechanically controls position or orientation of each activation element 104. The activation elements may also be electrostatically aligned using charge. In this case, each element includes an electret, a mechanism with permanent charge, or any other polar material that is responsive to an electric field. The electret may respond to the electric field by rotating, etc., in the same way that the previous embodiment responded to a magnetic field.

Figure 5A:
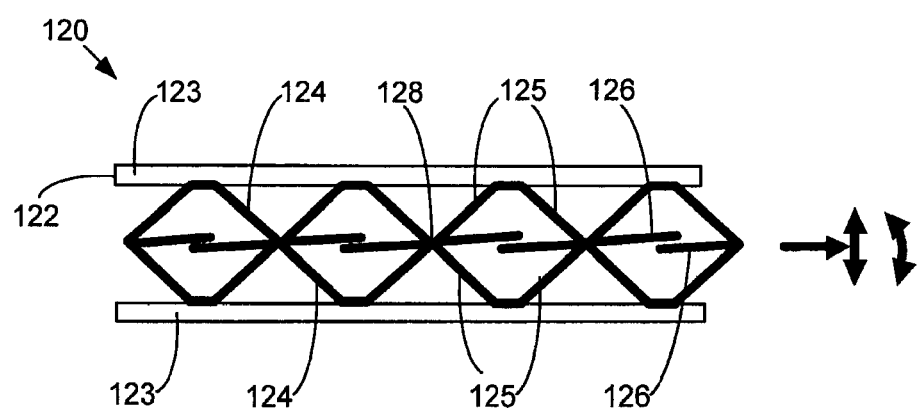
FIG. 5A illustrates a meta-material in accordance with another embodiment of the present invention.

FIG. 5A illustrates a meta-material 120 in accordance with another embodiment of the present invention. Meta-material 120 includes deformable structure 122 and activation elements 124.

Deformable structure 122 includes two compliant or deformable layers 123. Each compliant layer 123 has a stiffness that permits planar expansion and bending out of the plane when the activation elements 124 are not activated.

Each activation element 124 includes four rigid struts 125 and two stiff components 126. One end of each rigid strut 125 couples to either the upper or lower compliant layer 123. A joint 128 connects adjacent activation elements 124 and permits pivotal motion between adjacent activation elements 124. Joint 128 also permits pivoting between two rigid struts 125 and a stiff component 126 included in each activation element 124.

Stiff components 126 may be controlled to achieve two states: a) a free state in which left and right stiff components 126 are not coupled and free to slide past each other; and b) an activated state in which the left and right stiff components 126 are coupled together.

Cumulatively, meta-material 120 provides a truss-like structure that can be selectively engaged or disengaged, such as by clamping stiff components 126 together. When all stiff components 126 are free, a lateral force may move the left and right stiff components 126 relative to each other. This laterally squeezes or expands each activation element 124. Mechanical linkage between rigid struts 125 at joint 128 converts lateral motion into vertical motion for each activation element 124. Deformable structure 122 may also bend in this free state, to a limited extent.

Activation elements 124 include a mechanism that permits each activation element 124 to be locked in a current position or increase stiffness. In one embodiment, left and right stiff components 126 are activated using electrostatic clamping. In one clamping design, one of the components 126 includes an electrode and an insulating layer disposed thereon. The other member acts as ground. In another clamping design, each compliant 126 includes a layer of insulation and electrostatic clamping occurs across the insulation layer. Applying an electrostatic clamping voltage to the electrode fixes the stiff components 126 in a single activation element 124 together. This prevents lateral motion of the activation element 124, and prevents vertical motion due to the mechanical linkage at joint 128. This also prevents bending of deformable structure 122.

In another embodiment, stiff components 126 include an intrinsically adaptive or active material that can change stiffness of the linkage and thereby changing the stiffness of meta-material 120. For example, stiff component 126 may include an electroactive polymer that responds to electrical stimulus to change its stiffness, and that of meta-material 120. Other intrinsically adaptive or active materials that may be used for activation element 124 include piezoelectric benders with surface features similar to FIG. 3B that can form an interlocked pair when activated, thermally-controlled or shape memory alloy benders, and rigid elements where at least one has an electromagnet, for example.

In a specific embodiment, deformable structure 122 includes any compliant layer material, such as a rubber or elastomer or patterned polymer or metal. Rigid struts 125 may include a metal, a plastic, or any other rigid material. Stiff components 126 may include any materials used above with respect to the scale embodiments, such as a metal with a non-conductive coating (e.g., a non-conductive anodized coating), polymers with a metal sputtered on one side, carbon particles in a binder with a polyimide insulator, or any conductive material with an insulator.

Like many designs described so far, the truss meta-material 120 can be 3D or 2.5D. By 2.5D, it is meant that the structure has no differentiating features of interest in the third dimension; it may be of uniform size, such as made by extruding the 2D pattern of the figure in a third orthogonal direction. We also note that the basic structure of FIG. 5A can be stacked to form a thicker material.

Figure 5B:
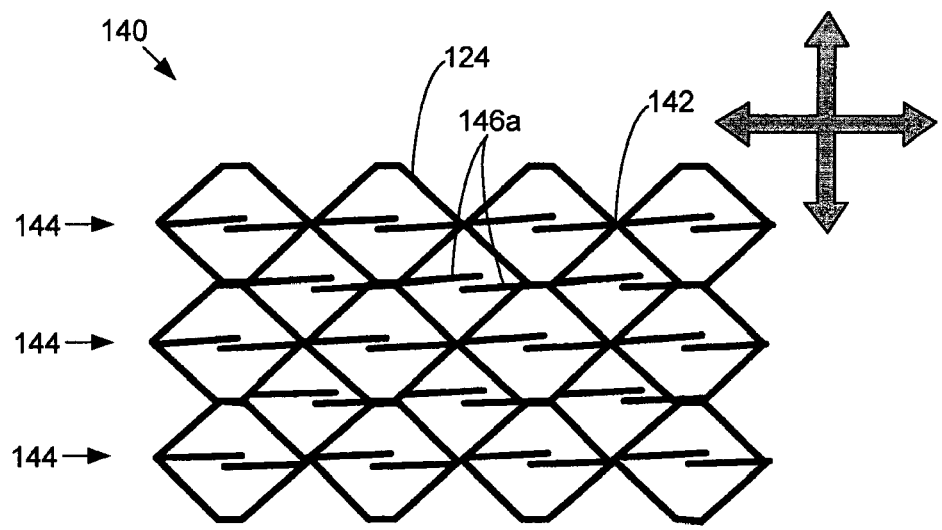
FIG. 5B illustrates a multilayer meta-material including the activation elements used in the meta-material of FIG. 5A.

FIG. 5B illustrates the activation element 124 of FIG. 5A included in a different deformable structure 142 for a meta-material 140 in accordance with a specific embodiment of the present invention.

In this case, deformable structure 142 comprises the arrangement of all activation elements 124 in a single integrated structure. More specifically, deformable structure 142 includes multiple rows 144 of activation elements 124, where the top of elements 124 in one row attach to the bottom of elements 124 in the above row. In addition, stiff components 146a are included in between rows at the point of attachment of two elements 124. Movement of any activation element 124 affects its neighbors when the activation elements 124 are in a free state.

Figure 5C:
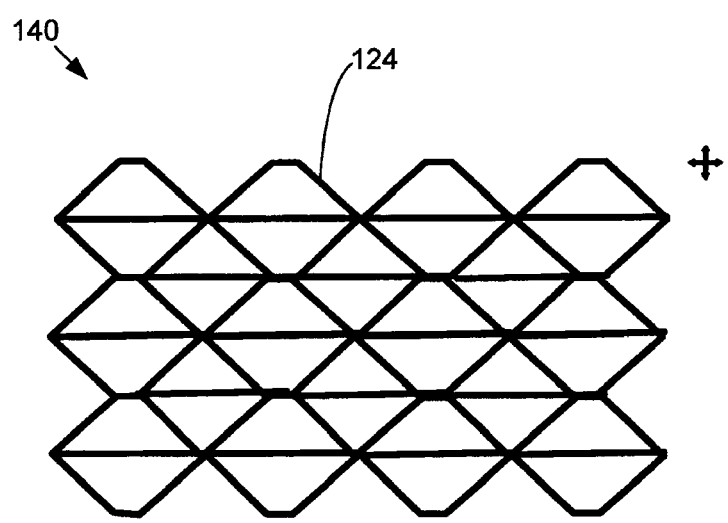
FIG. 5C shows the meta-material of FIG. 5B after activation of all elements.

FIG. 5C shows meta-material 140 after activation of all elements 124, which statically fixes deformable structure 142 and meta-material 140 in its current position. The meta-material 140 can be planar or extruded out of the page.

Meta-materials may also provide tunable bending stiffness control. In one embodiment, a meta-material provides bending stiffness control by providing the ability to clamp on multiple surfaces, such as both the upper and lower surfaces of a compliant layer.

As noted, meta-materials may control shape change. Active materials may also be incorporated into a deformable or reconfigurable structure in order to provide energy for the shape change.

Figure 7C:
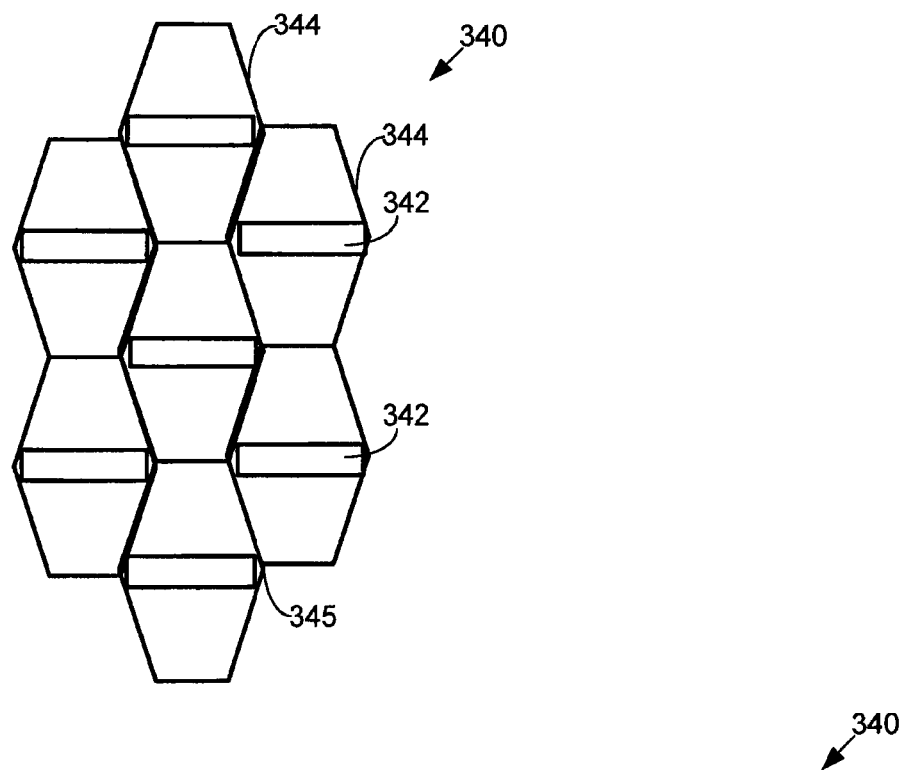
FIG. 7C illustrates a "snap-through" bistable meta-material in accordance with one embodiment of the present invention.

In one embodiment, a meta-material capable of such self-actuated shape change can use a snap-through or bistable mechanism in order to change between one shape to another (in either direction). FIG. 7C illustrates a "snap-through" bistable meta-material 340 in accordance with one embodiment of the present invention. Meta-material 340 includes actuation elements 342 and hexagonal structural elements 344.

Actuation elements 342 laterally expand upon application of electrical stimulation. In a preferred embodiment, actuation elements 342 include planar electroactive polymer actuators, such as dielectric elastomers. Further description of actuation of electroactive polymer actuators and devices is described in commonly owned U.S. Pat. No. 6,781,284, which is incorporated by reference herein in its entirety for all purposes.

Figure 7D:
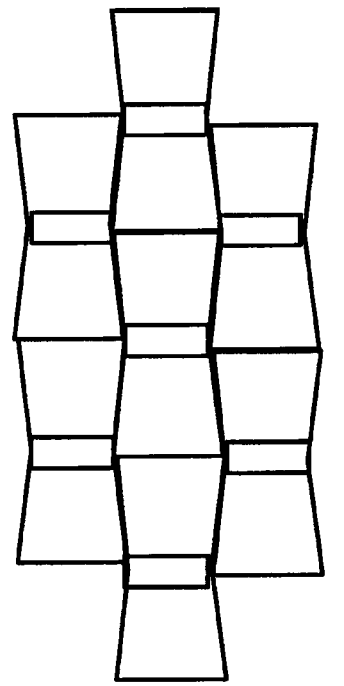
FIG. 7D illustrates the bistable meta-material of FIG. 7C after activation.

Actuation elements 342 are embedded in individual hexagonal structural elements 344, or 'cells', and span the width of each cell, as shown in FIG. 7C. When the electroactive polymer actuators are actuated, the resulting change in width of each hexagonal cell 344 snaps the cells into an "hourglass" shape, thus causing a large overall shape in the overall structure 340 as shown in FIG. 7D. Intermediate deformations are also possible.

Figure 7E:
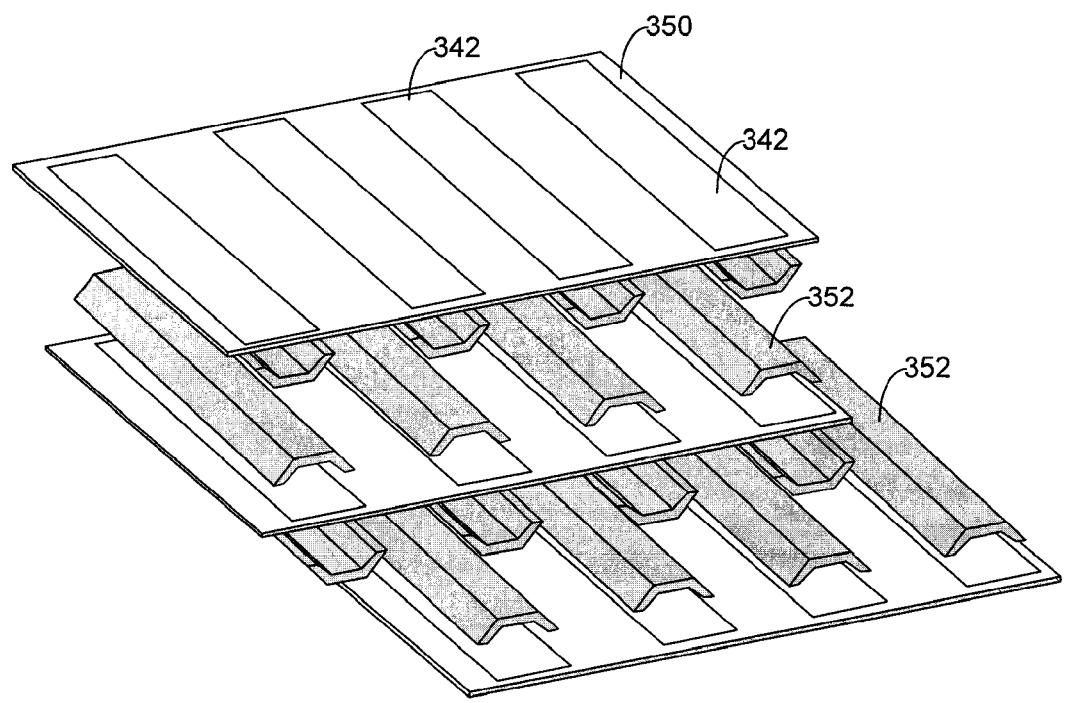
FIG. 7E demonstrates the bistable meta-material of FIG. 7C can be manufactured using a simple lay-up process.

FIG. 7E demonstrates how such a meta-material can be manufactured using a simple lay-up process. The actuation elements 342 can be manufactured in the form of sheet structures 350, as shown. These sheets contain regions of individually addressable actuation elements on a monolithic substrate. Further description of multiple electrode monolithic electroactive polymer actuators is described in commonly owned U.S. Pat. No. 6,664,718, which is also incorporated by reference herein for all purposes. These active layers are alternately layered with the half-hexagon structures 352 so that when attached in a stack they form a cross section as shown in FIG. 7C.

Figure 7F:
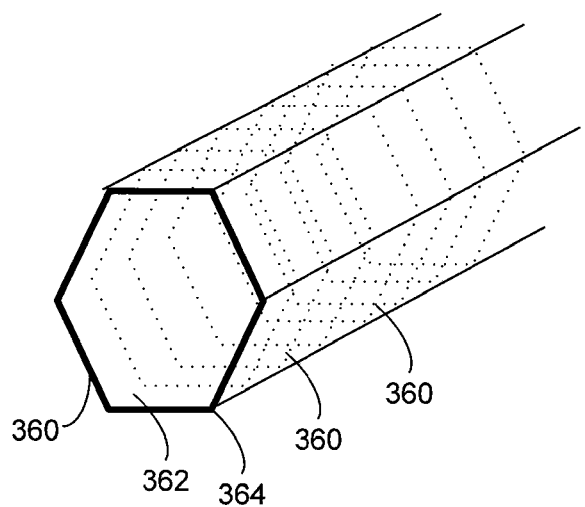
FIG. 7F illustrates a meta-material that includes a stack of planar "bow" actuators in accordance with one embodiment of the present invention.

A second configuration for bistable meta-material 340 includes a stack of planar "bow" actuators 360 (FIG. 7F) that each comprise an electroactive polymer 362 that spans and attaches to the inside of a flexible frame 364 (attaches about the perimeter of the polymer 362). Flexible frame 364 acts as a hexagonal linkage with joints at each corner. Further description of bow actuators is described in commonly owned U.S. Pat. No. 6,781,284 B1, which is also incorporated by reference herein for all purposes. When the bow actuator 360 is actuated, the overall area change is coupled to a change in the width of the cell. By alternately depositing the hexagonal linkage structure and planar actuators, a stacked honeycomb structure comprising several bow actuator structures may be fabricated. Such a stack of bow actuators 360 is shown in FIG. 7C.

Figure 7G:
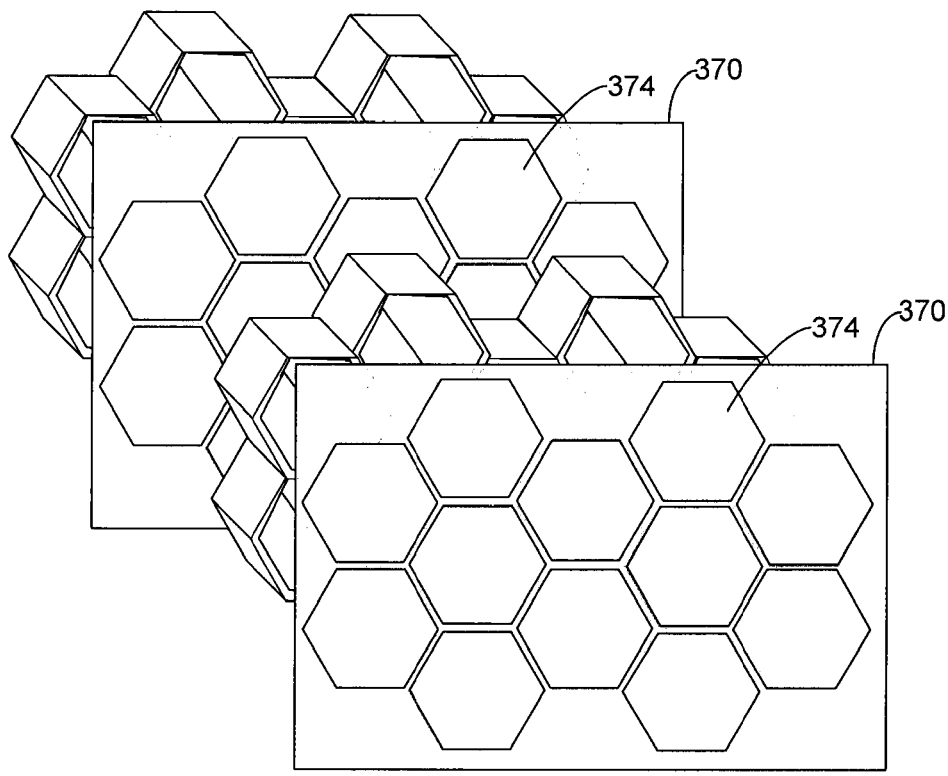
FIG. 7G shows many bow actuators of FIG. 7F grouped into a honeycomb structure and stacked in parallel.

Many bow actuators 360 can be grouped into a honeycomb structure and stacked in parallel as shown in FIG. 7G. Similar to the example shown in FIG. 7E, honeycomb electrodes and activation elements 374 are alternately layered as electrodes on sheets 370 of electroactive polymer. The electroactive polymer sheets 370 contain individually addressable activation elements 374 on a monolithic substrate.

Each individual cell of any of these embodiments may be individually addressable. This permits intermediate shape changes by only actuating a subset of the cells. In some designs, in order to achieve the ability to control the shape of sections of the material or the material as a whole, it the entire meta-material is segmented into distinct blocks so that there is not mechanical interaction between the blocks. For example, the honeycomb structures of the designs above may be segmented so that the deforming honeycomb structures do not all interact in unison. By controlling the shape of individual cells of the entire meta-material structure, it is possible to achieve an arbitrary desirable shape of the entire structure.

The shape of each cell affects the stiffness and damping properties of the cell in a particular direction. For example, a cell with walls that are nearly aligned in one direction will be stiffer in that direction than a cell with walls that are at large angles relative to that direction.

Figure 6A:
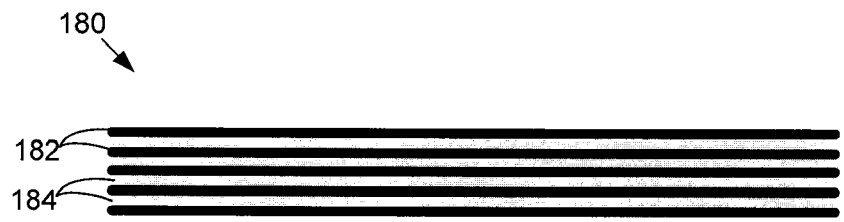
FIGS. 6A-6C illustrate a modular meta-material useful for controlling bending stiffness in accordance with a specific embodiment of the present invention.
Figure 6B:
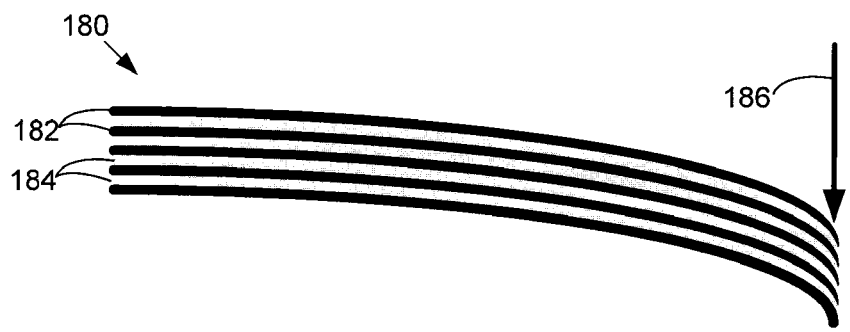
Figure 6C:
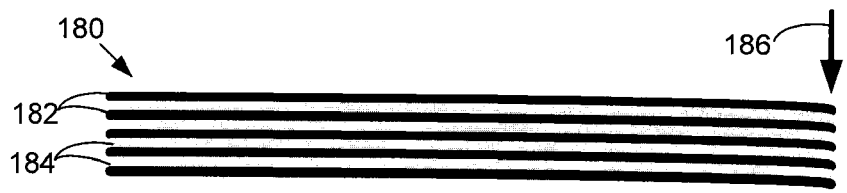

FIGS. 6A-6C illustrates a layered composite meta-material 180 in accordance with a specific embodiment of the present invention. Meta-material 180 permits bending stiffness control as well as the control of the shape of a flat surface.

Meta-material 180 includes multiple flexible layers 182 and activation layers 184. Each activation layer 184 is sandwiched between two flexible layers 182. In general, each flexible layer 182 includes a combined thickness and elastic modulus such that the layer may bend but is largely non-extendable. Activation layer 184 includes two states: a) a first state in which the activation layer 184 mechanically couples to its two neighboring flexible layers 182, and b) a detached state in which the activation layer 184 does not mechanically couple the two neighboring layers allowing shear between these two flexible layers. Activation layer 184 may then include any material that permits external control to couple and de-couple each activation layer 184 to its two neighboring flexible layers 182.

In a specific embodiment, flexible layers 182 include a thin conductive sheet (such as copper, aluminum or another metal), while activation layers 184 include a flexible dielectric (such as nitrile rubber). In this case, meta-material 180 uses two neighboring flexible layers 182 as electrodes to apply an electrostatic clamping voltage to the dielectric activation layer 184 disposed therebetween. This couples the activation layer 184 to its two neighboring flexible layers 182. Each layer 184 in meta-material 180 may be similarly activated. The entire stack of layers may also be activated simultaneously.

Before engaging activation layers 184, flexible layers 182 permit bending of meta-material 180 in response to an external vertical force 186, as illustrated in FIG. 6C. A single sheet (in cross section) of flexible layer 182 provides a bending stiffness for meta-material 180 relative to E, the elastic modulus of the material used in layer 182. Multiple de-activated layers 182 layered will together produce a bending stiffness for meta-material 180 relative to N×E, where N is the number of flexible layers 182. As shown in FIG. 6C, this still provides a relatively flexible bending beam. Force 186 may instead be a distributed force over the length of the beam or force combined with a torque. Several forces could introduce compound bending into the beam.

When an electrostatic clamping voltage is applied onto every activation layer 184, the layers 182 and 184 clamp together, which increases the bending rigidity of meta-material 180. More specifically, after activation, each activation layer 184 couples to both adjacent above and below flexible layers 182. This increases the aggregate bending stiffness of meta-material 180 since bending of meta-material 180 now requires shear of each connected layer 182 and 184. In a specific embodiment, the bending rigidity of meta-material 180 increases by a factor of about N3. This allows meta-material 180 to be flexible when de-activated, but stiff when activated. In some cases, the change in bending stiffness ratio from activated to de-activated may be N3:N, or N2:1. Any number of layers 182 and 184 may be used.

Component materials for meta-material 180 may be selected based on their material properties to produce a desired dynamic result. For example, steel may be used in flexible layers 182 to increase bending stiffness. Other suitable materials include flexible polymers with electrodes patterned on their surfaces, and carbon-fiber composite materials, for example.

In one embodiment, flexible layers 182 are coupled or otherwise attached such that they form a single structure for meta-material 180. For example, layers 182 may each attach to a plate on one end (or both). In another embodiment, meta-material 180 is a free-form structure, as shown. This permits the meta-material 180 to be bent and twisted as desired. For example, meta-material 180 may be externally manipulated (bent, twisted, etc.) using an actuator, or manually. At any particular shape, activation using electrostatic clamping voltages will lock the current shape of meta-material 180.

In a specific embodiment of the design shown in FIGS. 6A through 6C, the activation layers 184 include 0.004" thick nitrile rubber (for example, nitrile rubber used in Safeskin brand nitrile gloves made by Kimberly-Clark Corporation, Roswell, Ga. 30076 USA). The flexible layers include 0.002" thick brass sheets. 10 centistoke silicone oil can also be used to help prevent separation of the layers, though depending on the application and external loading this may not be necessary. Clamping voltage may range from about 1000 to about 1500 V DC.

Other activation mechanisms and systems may be used for meta-material 180. In one embodiment, each flexible layer 184 includes a compliant polymer or elastomer. Activation layer 184 may achieve a change in attachment by clamping, a shape change in a viscoelastic material (e.g., using an active material such as an electroactive polymer), or by squeezing the layers 184 together. In all these instances, there will be increased shear forces in the activation layer 184 when the composite meta-material bends. In another embodiment, the activation layer includes a layer that swells such that, before activation, the activation layer 184 only couples to one flexible layer 182. In this case, each activation layer 184 does not experience a large amount of shear deformation before activation. After activation, the activation layer 184 couples to both adjacent flexible layers 182, which now induces shear stresses in the activation layer 184 when the composite meta-material bends. Materials such as polymer gels, thermally expansive materials could be incorporated into the activation layer 184 to provide this functionality. Activation layer 184 could also incorporate active materials such as electroactive polymers or piezoelectric ceramics that are attached to mechanisms that allow for large out-of-plane deformation. For example, Expansion of electroactive polymer sheets could squeeze a thin layer of flexible polymer that buckles and presses on neighboring layers 182. Activation layers could also be composed of magnetorheological or electrorheological fluids. These fluids change form a low-shear stress state to a much higher shear-stress state upon the application of a magnetic and electric field, respectively.

Meta-materials 140 and 180, like many designs described herein, are modular. This allows the basic pattern to be repeated in both the planar direction or out-of-plane direction (stacking) to produce meta-materials with any suitable size, length, or shape.

Some meta-materials also employ shape changes to affect mechanical property changes. FIG. 7A illustrates a beam 160 that changes shape in accordance with a specific embodiment of the present invention. Beam 160 includes a compliant layer 162 and flexible but non-extendable material 164 disposed on the bottom surface of compliant layer 162.

In a specific embodiment, compliant layer 162 includes an electroactive polymer. An electrode 166 is disposed on the top and bottom surfaces of the electroactive polymer. Actuation of the electroactive polymer using electrodes 166 causes the compliant electroactive polymer to arch as shown in FIG. 7B. Alternatively, meta-material 160 may not include an electroactive polymer and relies on external forces (such as electrostatic attraction to a nearby flat surface) to produce a desired shape change.

Triggering activation of beam 160 (either by applying a voltage across an electroactive polymer or removal of electrostatic attractive forces that cause the beam to conform to a flat surface) causes it to attain a more rigid position, such as the position shown in FIG. 7B. This increases stiffness of beam 160 in response to loads both along and perpendicular to the bending axis of the beam. For example, beam 160 will deflect less in response to a downward force applied at its distal end.

The beam of FIG. 7, while effective in changing properties is a simple example of how low-energy shape change can lead to a great change in one or more mechanical properties. In order to form a meta-material, this basic beam structure may be incorporated as a building block element of other structures. For example, an array of such beams standing on end may be sandwiched between two rigid plates. The resulting layered structure would be much stiffer when the elements were activated to a state shown in FIG. 7B. In another embodiment, the beams may be attached along one edge to a flexible surface. This surface can bend when the beam is in the unlocked state of FIG. 7A but not when the beam is in the locked state of FIG. 7B.

Meta-materials formed from beam 160 thus demonstrate another aspect of the present invention: using a shape change to vary a mechanical property and locking the meta-material at the new shape. In this case, the change in shape increases vertical stiffness of the bending beam.

While meta-materials formed from beam 160 employ a simple structure and simple shape change that is well suited for illustrative purposes, the present invention is not limited to such simple design and shape changes and may include more complex deformable structures before and after activation.

Shape change (whether it be the desired change in shape of the meta-material or the change in shape of an element within the meta-material) need not result only from forces or actions created internal to the meta-material. For example, one application below describes the use of meta-materials for shape changing wings on an airplane. In this case, the meta-material is de-activated (put into the low-stiffness state), moved using a suitable actuator (or the wind), and then activated at some desired shape, position or configuration. In some cases, when the wind is turbulent, de-activating the material only when the resulting wind pressure acts in a desired direction produces a seemingly self-actuating system.

Any suitable actuator may be used to move the object and deform or reshape the meta-material. Motors, pneumatic cylinders, and solenoids are suitable for use in many systems. In one embodiment, an electroactive polymer transducer is used to deflect a meta-material while the meta-material is in a de-activated state. Electroactive polymers are a class of compliant polymers whose electrical state changes with deformation. Actuators including an electroactive polymer may come in a wide variety of shapes and sizes and may be tailored to a specific application or design. Exemplary electroactive polymers may include electrostrictive polymers, dielectric elastomers (a.k.a. electroelastomers), conducting polymers, IPMC, gels, etc. Further description of electroactive polymers suitable for use with the present invention is described in commonly owned U.S. Pat. No. 6,628,040, which is incorporated herein by reference in its entirety for all purposes. Other suitable actuators may include the active or intrinsically variable materials described above. Electrostatic or electromagnetic forces, similar to those that may be used for clamping, may also be used to provide actuation for shape control. For example, two overlapping layers with bands of electrodes or electromagnetic regions can be made to slide relative to one another by sequentially alternating the voltage of the bands in much the same way that a linear motor moves the slider relative to the stator. Such linear motors based on flat sheets that slide relative to one another are known to one of skill in the art. These motorized layers can be attached to the deformable structure of a meta-material or take its place completely.

Properties and Performance

A meta-material permits dynamic control of one or more mechanical properties. Controllable mechanical properties include stiffness, damping, elastic or plastic strength, yield strength, tensile or compression strength, shear strength, elastic modulus, toughness, tear resistance, maximum elongation, strain to failure, energy absorbed until failure, Poisson's ratio, creep, fatigue, tribology, shear modulus, resilience, acoustic transmissivity, damping, mechanical loss factor, hardness, impact resistance, shock resistance, and shape.

As described so far, meta-materials described herein are well suited for stiffness control. For activation elements that employ electrostatic clamping, as long as static clamping and frictional forces between the activation elements are larger than an external force trying to pull them apart, the clamping is effective (i.e., no slippage occurs). This clamping causes the stiffness of the meta-material to be approximately equal to the stiffness of the rigid component material. Some compliance may be introduced by shear deformation of a compliant layer (if included), but this compliance is small when a thin elastomer layer is used. Scale-insulated designs do not have this compliance issue. In some cases, the insulation in this type of design can in fact be stiffer than the core scale material.

Rigid activation elements on a compliant planar structure and having activation control in two dimensions permit controllable stiffness in both in-plane directions. This allows dynamic directional control of planar stiffness, i.e., stiff in one direction while compliant in another direction, and then a change to the opposite stiffnesses in each direction. Bending and planar stiffness may also be independently varied for some meta-material designs, e.g., by controlling the relative stiffness on opposite sides of a compliant layer.

The present invention also permits variable and dynamic control of stiffness of a meta-material between minimum and maximum extremes during usage. In one embodiment, tunable (dynamic and variable) stiffness is achieved by selectively activating some but not all activation elements to effectively provide a variable stiffness. Alternately, damping control of the structure may be achieved when a lower voltage is used for electrostatic clamping embodiments so that the activation elements can slide under load but still resist an applied force by a controlled amount. In some embodiments, such as those that use magnetorheological or electrorheological fluids, changing the degree of activation by varying the voltage can also directly affect stiffness change.

Changes in stiffness provided by a meta-material of the present invention can be quite dramatic. For example, a compliant layer with an elastomer substrate such as silicone (with an elastic modulus of about 1 MPa) and scales of 6061-T6 aluminum (with an elastic modulus of 70 GPa) may theoretically change in stiffness by a factor of 70,000. In one embodiment, a meta-material is capable of changing stiffness by factor of greater than 100 times its original stiffness. This is useful in vibration or noise control where matching (or avoiding) the resonance of a frequency change by a factor of 10 requires a change in stiffness by a factor of 100. Materials for morphing structures will also benefit from a large change from rigid to compliant, and back to rigid. In a specific embodiment, a meta-material is capable of changing stiffness by factor of greater than 1000 times its original stiffness. An arbitrary stiffness can be selected between two extremes (e.g., by controlling the number of elements that are activated across the surface of an electrostatically clamped meta-material). In another embodiment, before and after stiffnesses are used to characterize a meta-material. A meta-material including a stiffness before activation that is less than about 1 MPa and a stiffness after activation greater than about 1000 MPa is suitable in many applications. In a specific embodiment, a meta-material includes a stiffness before activation that is less than about 10 MPa and a stiffness after activation that is greater than about 100 MPa. In some cases, a meta-material may start at about 100 MPa and convert to about 10 GPa after activation.

While the present invention so far has been described primarily with respect to dynamically varying stiffness in a meta-material, the present invention is not limited to controlling this specific mechanical property.

Meta-materials also provide active and dynamic damping control. We have noted that damping provided by a meta-material including electrostatic clamping may be actively controlled by intentionally allowing slippage of activation elements. Thus, the electrostatic clamping voltage may be reduced to an amount that allows sliding of the activation elements. In other words, an electrostatic clamp is applied that is not strong enough to withstand an external force being damped. This partial clamping approach allows for controlling the effective damping of a structure including the meta-material. Controlled damping may be achieved using any of the electrostatic clamping meta-materials described above. For example, partial clamping of stiff components 126 in meta-material 120 (FIG. 5A) allows sliding that produces an amount of damping related to the degree of clamping.

Controlling the amount of shear deformation of one or more viscoelastic layers in a meta-material also permits damping control. To increase the damping of a bending beam, one may trap a layer of viscoelastic material between flexible layers 182 of meta-material 180 (FIGS. 6A-6B) so that the shear forces on this layer are greatly increased and consequently this layer adds a significant amount of damping to the overall structure.

Meta-materials may provide independently controllable stiffness and damping. For example, a composite may include separate layers to control stiffness and layers to control damping. As noted above, if activation results in a binary change in stiffness or damping, then activating a subset of the total number of activation elements may provide fractional control.

Meta-materials may also be designed to permit variable toughness (energy absorbed before failure) or resilience (energy absorbed before plastic deformation). Some embodiments of the present including aluminum may provide greater toughness or resilience than aluminum itself. For example, when a meta-material fails (releases electrostatic clamping) in tensile load, the failure is not catastrophic. The meta-material may be configured to re-clamp at a slightly extended length and continue to function at the clamping stiffness. By repeatedly allowing the material to release and re-clamp, the meta-material dissipates a large amount of energy. Thus, a meta-material may enhance not only the stiffness of a device, but also its resilience. Even of the material repeatedly fails, once the load is removed and the material is deactivated, it can elastically return to its original shape without damage.

In one embodiment, a meta-material is configured in an object to support structural loads. This may reduce overall mass of an object by reducing the mass of other structures used to support structural loads. Depending on the object and design, the meta-material can support a bending load by providing tensile and compressive in-plane stresses and torque, carrying shear flow as a part of a closed torque box, etc.

External Control

Implementation of a meta-material may employ external control of some type. This may include any hardware needed for communication with the activation elements and any circuitry or logic for implementing control.

For electrostatic clamping embodiments, at the very least, a minimum amount of control hardware (wires, etc.) and circuitry is needed to provide remove electrostatic clamping voltages to and from the activation elements. In one embodiment, a meta-material includes separate control for each activation element. In another embodiment, subsets of activation elements are commonly addressed and controlled (e.g. using a common electrode). Logic of varying goals and complexity may also be used to control the activation elements and regulate the mechanical property of interest.

In general, the energy required to engage a set of activation elements to change the meta-material and mechanical property ("energy of activation") can be small relative to the resulting energy performance of the meta-material. In many cases, elastic and damping energy is born by the aggregate meta-material. For example, once an activation mechanism engages a rigid activation element, it is the energy of deformation of a meta-material or structure that determines the mechanical property and not the energy of activation. Control can thus be made and maintained with little energy expenditure, e.g., input electrical energy. Since activation is only required to make small or low-force motions or provide clamping, which requires little energy in many cases but produces dramatic mechanical properties, the present invention also then provides energy efficient mechanisms to affect large changes in a mechanical property.

The electrical power needed to hold electrostatic clamping embodiments is relatively minimal, since the effect is electric-field-based and does not require significant amounts of current to flow. Power consumption for electrostatic clamping depends on the insulation thickness, the clamping pressure, and the insulation resistivity. For example, for a 1 m2 surface that is clamped with 10% overlap and has an insulation thickness of 10 μm, resistivity of 1013 ohm-m (silicone, silicon dioxide, or other insulators, for example), and a field of 300 V/μm (sufficient for about 1 MPa clamping pressure with a dielectric constant of 2.7), the power required to hold full load is only 4 mW. This example is only illustrative; other, better insulators with thinner coatings may reduce power consumption. Also, alternative designs that use mechanical interlocks can use little or no voltage in the clamped state (see FIG. 3B). From a basic perspective, the electrostatic clamping activation elements act as a capacitor, so some finite amount of energy may be needed to apply the clamping voltage. In one embodiment the energy applied to the meta-material is recovered when the material is deactivated. Embodiments that use electrostatic clamping are a highly reactive (capacitive) electrical load. Electrical circuits that can recover energy from a capacitive load are known to those skilled in the art. In one embodiment, electrostatic clamping relies on high voltage. In a specific embodiment, the clamping voltage is above about 1 kV. Other voltages may be used, as appropriate. Depending on the materials used, electrostatically clamped embodiments employ low-current, high-voltage operation (often with low leakage current) that minimizes the mass of the power supply, electrical wiring, and connectors. This provides many energy efficient meta-materials.

Several factors will influence an available electrostatic clamping force, as well as the required power. These parameters include a) the insulating or dielectric material and its thickness; b) the activation element material, compliance; and geometry, and c) the drive circuit (AC or DC excitation). Several suitable insulating and dielectric materials include polyimide and polyvinylidene fluoride (PVDF). In addition, more conductive materials such as nitrile rubber and thermoplastic polyurethane may also be suitable for some applications. Surface roughness and scale compliance may also increase the available electrostatic clamping force.

The present invention may use AC or DC excitation. Depending on the materials being used and electrical energy supply, the force of electrostatic clamping driven by a DC signal (or any other non-reversing voltage) may reduce over time due to parasitic charging of the surroundings and charge migration within a dielectric. Use of a bipolar (i.e. going positive and negative) AC signal instead of a DC signal may eliminate dielectric charging in these instances. With an AC signal, the clamping force goes briefly to zero each time the voltage changes polarity. In one embodiment, a meta-material includes a set of mechanically redundant activation elements. By using mechanically redundant activation elements, a meta-material may eliminate slippage when the AC signal goes through the zero-voltage point of some subset of the activation elements. In another specific embodiment, a meta-material includes redundant clamping activation elements that are arranged in parallel. If some of the redundant activation elements are driven with a signal that is 90 degrees out of phase with the other AC signal, then at least some of the activation elements are always clamped. In another embodiment, the electronic speed of switching polarities may be so fast that the mechanical system doesn't have time to slip (i.e. the inertia prevents any significant motion before the field changes polarity and re-clamps). In a specific embodiment, an excitation frequency above about 1 Hz is used. Other AC frequencies may be used.

In addition, the present invention also permits variable control of a mechanical property between its minimum and maximum extremes. For example, many electrostatic clamping embodiments permit clamping voltages between the minimum and maximum extremes (e.g., to permit damping). The control electronics may then include conditioning electronics to facilitate such control and logic to implement variable control. Variable or binary control may include open loop control, closed loop control with active sensing, etc.

Figure 12:
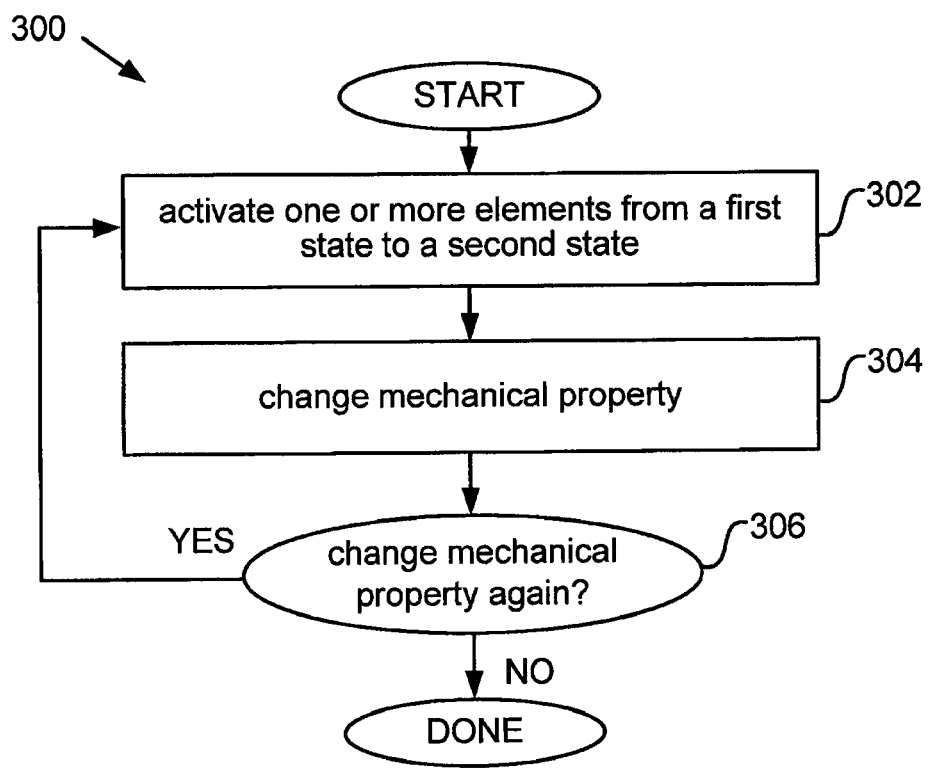
FIG. 12 illustrates a process flow for altering a mechanical property in a meta-material in accordance with one embodiment of the present invention.

In one aspect, this invention relates to a method for changing a mechanical property of a meta-material. FIG. 12 illustrates a process flow 300 for altering a mechanical property in a meta-material in accordance with one embodiment of the present invention. The meta-material includes a deformable structure and a set of activation elements coupled to the deformable structure.

Process flow 300 begins by activating one or more activation elements from a first state to a second state (302). Activation may include applying an electrostatic clamping voltage to electrostatic clamping activation elements. A magnetic field may be altered to activate one or more magnetic-based activation elements. In general, activation will employ any suitable steps as determined by the activation mechanism used in meta-material.

The first or second state may include a fully 'on' or 'off' state, or some other partial state therebetween. Many meta-materials offer tunable mechanical property changes based on varying input. For example, voltage applied to an activation element may be regulated at stepwise input levels via a feedback control loop to achieve a desired level for damping or toughness. Alternatively, the position of an activation element may be controlled via a magnetic field to permit a number of positions between two position extremes that affect stiffness or damping.

The mechanical property changes in response to acquisition of the second state by the one or more activation elements (304). In one embodiment where the mechanical change is a stiffness change, the activation elements include a stiffness or modulus of elasticity greater than that of the deformable structure. In this case, multiple rigid activation elements may link together to increase aggregate stiffness of the meta-material. In one embodiment, the activation element is engaged to change a meso-scale geometry or connectivity of the deformable structure and thereby change the viscoelastic properties of the meta-material composite. Stiffness changes are well suited for noise, vibration and shock suppression and control. For example, activation elements may be triggered such that an object that includes the meta-material or avoids a resonance frequency witnessed by the object without the stiffness change. Alternatively, the meta-material may be used in an object as a dynamic vibration absorber and the stiffness change causes the meta-material to match a resonance frequency witnessed by the object and absorb energy at the resonance frequency.

Process flow 300 then determines if another change is desired (306). In electrostatic clamping applications where a mechanical property is tunable for example, the activation elements may be partially activated using a first voltage between the permissible minimum and maximum voltages. The voltage—and mechanical property (e.g., damping, stiffness)—may then be increased or decreased as desired.

While the present invention has primarily been described with respect to changing a mechanical property of the meta-material, it is understood that the present invention may also be used to control a mechanical property of a device, object or structure that includes a meta-material. Thus, process flow 300 may also be applied to control a mechanical property for a device, object or structure by controlling one or more active elements in the meta-material.

Figure 13:
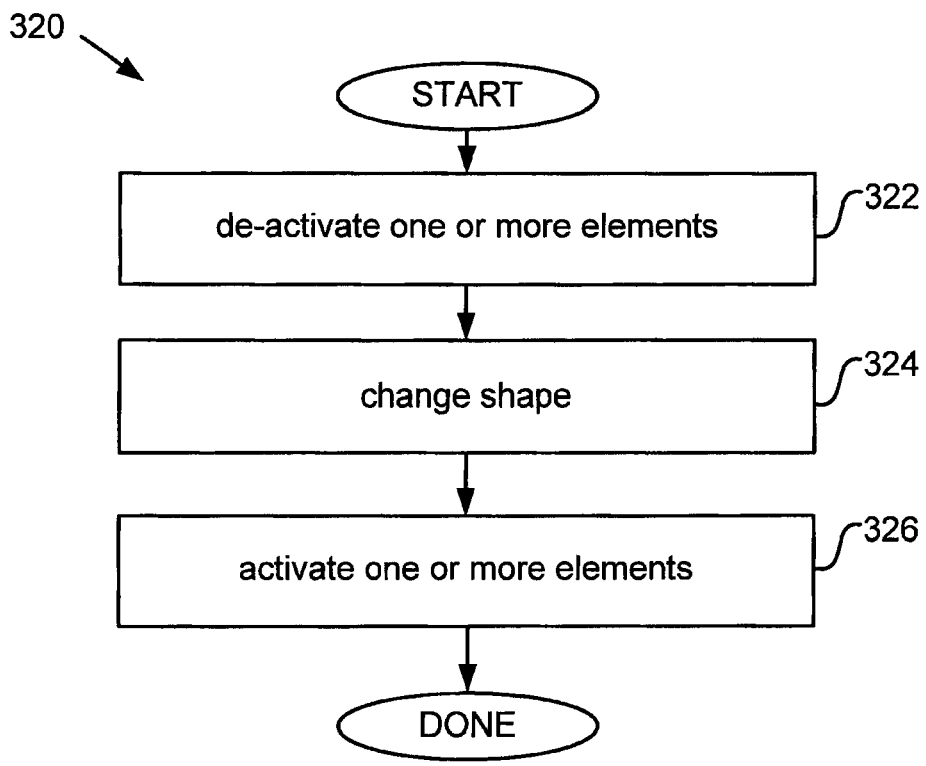
FIG. 13 illustrates a process flow for changing shape of a meta-material in accordance with another embodiment of the present invention.

In another embodiment, the present invention relates to a method for changing shape of a meta-material or an object. FIG. 13 illustrates a process flow 320 for changing shape of a meta-material in accordance with another embodiment of the present invention.

Process flow 320 begins by at least partially de-activating one or more activation elements. De-activation in the sense may include full de-activation, or partial de-activation to some intermediate state between on/off extremes for the activation element. The elements may be de-activated to reduce stiffness, damping, or some other mechanical property of the meta-material or object, or otherwise change connectivity or shape of the meta-material. At the least, the activation elements will be de-activated such that the meta-material is responsive and compliant to an external force that moves the deformable structure.

Shape for the meta-material or object is then changed (324). This may include applying a force to the deformable structure to change shape of the meta-material. In one embodiment, environmental forces are used to change shape of the device. For example, an endoscope or catheter including a meta-material may be passively guided by the channels in which it navigates. When it is desired to steer the endoscope in a certain direction, certain regions of the meta-material are activated so that the device can only bend in the desired direction. This allows an environment to do work by controlling stiffness by unlocking (de-activating the meta-material to a point where it is compliant) and locking (activating the meta-material to a point where it is stiff relative to input forces) the meta-material at desirable times. This also permits using turbulence to move a fin in an air stream. In another embodiment, manual forces are used to change shape for a meta-material, as we described above.

One or more of the active elements are then activated (326). The activation may increase stiffness or otherwise change connectivity or shape of the meta-material. In addition, activation may stop at some intermediate position for the mechanical property less than the maximum mechanical property permitted for the meta-material.

Another embodiment of the invention relates to a method of absorbing energy. The method comprises changing one or more mechanical properties of the meta-material according to the energy absorption needs of an application. Once the mechanical properties have been set, a force is applied to the meta-material such that the deformable structure deforms. In ballistics and other impact applications, combining both high stiffness of the activation elements and high ductility of the compliant substrate may increase toughness of a meta-material. Thus, meta-material stiffness may be raised by activation. The deformable structure is then stretched at the higher stiffness. Alternatively, the meta-material may be used to change stiffness and/or damping to deliberately excite an object used as a tuned mass-damper or energy absorber in a vibrations application. The present invention also allows the mechanical properties of a meta-material or structure to be tuned for vibration or noise isolation when the frequency spectra of the disturbance input varies. Variations in stiffness over a single cycle of oscillatory motion (vibration) can also be used to damp such vibrations.

Applications

The ability to actively control or modulate mechanical properties such as the elastic and viscoelastic properties of a material or structure is useful in many applications. Indeed, the present invention represents a breakthrough technology because a meta-material fundamentally changes the paradigm of materials having a fixed set of mechanical properties post-production. In most engineering fields, an advance in materials technology has enabled new applications.

One example is an athletic or medical brace that can switched from soft and flexible to hard and stiff. Another example is footwear where springiness vs. absorption can be controlled. The ability to vary from flexible or stretchable to relatively rigid may also be incorporated into fabrics to be used in clothing or footwear with adjustable fit. The fabrics could also be incorporated into tents, reflectors, aircraft or watercraft skins where it is desirable to control the fit or compliance of the skin Such skins with controllable mechanical properties may be used in morphing structures such as morphing aircraft wings. In addition, the ability to modulate elastic and viscoelastic properties is useful vibration control systems such as for automobiles to vary the response based on different driving conditions.

The development of air and space vehicles has been tied to materials developments. From the first wood and fabric materials to high speed, high-strength metal alloys and to modern-day composites, the development of new materials has enabled improvements in the performance of military and commercial aircraft. Twentieth century composites, with their directional stiffness and strength properties, provided a degree of freedom to aircraft designers over the last century—specifically, tailorability. Using composites, a designer could design aircraft structures with directionally variable properties to efficiently carry loads that are not directionally uniform. These properties have led to 10-20% weight savings in aircraft structures and have enabled the design of aircraft such as the forward swept X-29.

The present invention provides another degree of freedom: dynamic material performance. Just as composite materials whose mechanical (e.g., stiffness and damping) properties can be selected by design allowed a revolution in aerodynamic structures, a new generation of materials whose material properties can be actively controlled enable a new generation of aerospace structures.

Aircraft, such as unmanned air vehicles (UAVs), are playing an increasingly important role in aerospace applications. Currently, aircraft are designed for optimal flight in one particular flight regime. To minimize fuel consumption, low-speed surveillance aircraft have long narrow wings with no sweep. In contrast, high-speed attack aircraft (and highly maneuverable combat aircraft) include shorter-span, long chord wings with a large amount of sweep to reduce drag and increase aerodynamic efficiency. While some current aircraft are capable of minor variation in geometry, such as controlling the angle of wing sweep, the ability to change or "morph" between two very different platforms and wing shapes has not been achieved.

The present invention enables an aerodynamically efficient aerial vehicle capable of shape change. In one embodiment, an aircraft including a morphing wing with a meta-material component is capable of undergoing large deformations that are used for significant shape change, while supporting aerodynamic and structural loads. For example, one meta-material component may be an aircraft skin including electrostatically clamped rigid scales on a compliant substrate. The aircraft skin can change from rigid (by clamping the activation elements) to compliant (by releasing one or more activation elements) when desired. If a component or meta-material skin is always stiff (to meet aeromechanical load requirements), then shape change will use excessive energy and the morphing actuators will be large and heavy. Conversely, if the skin is always compliant it will not be able to resist mechanical loads. These conflicting requirements are accomplished with a meta-material component or skin whose stiffness can be controllably changed.

It may also be desirable to morph a structure in a partially clamped modes when it is useful to resist loads. This partial clamping approach allows for controlling the effective stiffness and damping of the structure. Controlling damping could suppress flutter or other undesirable motions (particularly during morphing) in an aerodynamic environment. For aircraft applications, the meta-material component or skin is also suitably tough and lightweight (particularly of use in smaller unmanned air vehicles). In one embodiment, the skin provides the requisite shear stiffness and bending stiffness for anticipated flight maneuvers when the activation elements are locked, and permits morphing during flight such as level flight.

A meta-material skin may be flexibly used in different parts of an aircraft. For example, a meta-material skin may be applied on a wing surface of the aircraft to change the aerodynamic characteristics and performance of the wing. Alternatively, a vertical tail may include a meta-material whose aerodynamic profile and/or size may change. In one embodiment, a morphing wing provided by the present invention includes a smooth surface to achieve good aerodynamic efficiency. Thus, the skin may undergo large deformations for radical shape change, while supporting aerodynamic loads, and maintain a smooth surface. In many designs, the meta-material skin also supports structural loads, thereby reducing the mass of the aircraft.

Other applications that could benefit from morphing include deployable or reconfigurable space-based mirrors and arrays. The meta-materials may also be used in an automobile body that can change shape. For example, an automobile panel may change to a more aerodynamic shape.

The present invention is also well suited for application in noise, vibration and shock suppression and control. Many applications demand lightweight and compact means of damping noise and vibrations serviceable by the present invention. In some cases, one would like to maximize damping in a structure. In more complicated structures, it is sometimes desirable to change both stiffness and damping to avoid exciting certain resonant modes or deliberately excite others (such as for a tuned mass-damper). If the frequency spectra of the disturbance input varies then vibration or noise isolation can be achieved by tuning the properties of the meta-material or structure itself.

Such a meta-material finds use as a surface panel in helicopter, tank or other land vehicle, for example. At certain frequencies, determined by the blade speed in the helicopter or the terrain in a tank, conventional panels can vibrate excessively and radiate significant noise (similar to the vibrations on a dashboard of a car driving on a dirt road). A meta-material panel material integrated into these structures reduces the vibrations, thus making the vehicles less noisy and more rider friendly. In other cases, it is desirable to excite a meta-material panel at an anti-resonance to cancel vibrations of the aircraft or vehicle structure. The stiffness may vary over a wide range in order to adapt to a range of input frequencies (the resonant frequency is proportional to the square root of the disturbance frequency). In these applications, weight and space is at a premium so the present invention offers a multifunctional panel—both a structural and active vibration control material.

Such weight-and-space-saving vibration canceling structures are useful in space applications. Structural skins or supporting truss structures used in morphing space structures may include adaptive meta-materials described herein. Existing space structures may benefit from adaptive composites that minimize vibrations during deployment or aiming of antennae or solar arrays, for example. The Canadarm can also use vibration and damping improvements provided by a meta-material skin described herein. Since the arm can hold relatively large payloads, a wide range of dynamic adjustment is needed. Vibration and noise canceling structures may also be integrated into a cargo bay or another portion of the space shuttle to minimize shock and acoustic damage to sensitive payloads during launch and engine burns.

In general, an adaptive meta-material may be used to control damping in response to planar stretching or bending of any deformable structure. Thus the meta-material may be included as a part of an overall vibration control system. The resulting structure may be considered a solid-state material whose stiffness and damping can be actively controlled. For example, the present invention also enables beams with inherent vibration control. Such beams are very useful in a wide array of applications. Meta-materials claimed herein may also replace variable-impedance automotive suspensions that currently employ harder-to-control, leak-prone, and environmentally sensitive magnetorheological and electrorheological fluids.

Meta-materials described herein may also be used in biomimicry and human interaction applications such as adaptive prosthetics, orthotics and robotics. In a specific embodiment, a meta-material is used to modulate joint stiffness and damping in a prosthetic and orthotic device to provide the user with a more efficient and stable gait or dexterity over a wide range of terrains and conditions. Meta-materials that allow electrical control of stiffness and damping properties may address the shortcomings of existing prosthetic and orthotic devices. For example, meta-materials do not require coils as do conventional electromagnetic and magnetoreheological devices. Since they are entirely solid, they cannot leak and are relatively insensitive to temperature changes. In addition, electrostatically clamping meta-materials are relatively light and energy efficient because their control is based on an electric field. The materials can be formed into thin sheets, so that they can be used with form-fitting orthoses as well as prostheses. These thin structures may also form the basis of an adaptive socket whose size and shape can be adjusted by the user according to preference. In addition to prostheses and orthoses, these controlled-stiffness materials may be applied to other medical needs. For example, they may be used to make adaptive casts, braces or splints that can be readjusted or loosened to allow for more comfort when resting or changes in the desired support or joint position during the healing process. This mechanically adjustable braces and splints thus provide adaptable protection in addition to motion.

The present invention is also well suited for use in high-energy absorption applications. These applications benefit from a material with high toughness, large ductile strain to failure, and high elastic modulus. In this case, a meta-material combines the strengths of a metal (or another rigid component) with the ductility of a compliant layer. Ballistics, crash protection, and high-speed impact applications represent exemplary applications where meta-materials of the present invention find use as dynamic and high-speed energy absorbers.

In energy absorption applications, the meta-material may be temporarily set to a high elastic modulus. When the stiffness due to the elastic modulus has been overcome, the meta-material may then let one or more activation elements slip (or otherwise let the compliant layer deflect), reapply the activation voltage and absorb energy elastically at the renewed and high elastic modulus. This continual slippage and re-activation of high elastic modulus allows an extended strain to failure, where significant energy is absorbed over stepwise periods of temporary high modulus.

The ability to select the energy absorption characteristics of a meta-material allows for greater crash protection for vehicles, as well as the occupants. For example, for a car including a meta-material and involved in a crash, sensors indicating the location of the impact could communicate with a computer that determines the best pace for the meta-materials to deform and absorb energy or maintain rigidity. Similarly, if an unmanned vehicle crashed, the meta-material could absorb energy at certain locations and elastically recover its shape following the crash.

The ability to control the voltage at which electrostatically clamping activation elements slide is also useful for maximizing energy absorption as applicable to armor. In a specific embodiment, increased energy absorption is achieved by allowing sliding just below a failure point of the electrostatic clamping. In effect, the meta-material combines the strength of a rigid material with the elongation of an elastic substrate. In this way it is possible to produce materials with greater resilience or toughness. This ability not only protects the armor, but also protects the wearer from second or third impacts.

Flexible clothing that can readily switch to hard armor ballistic characteristics represents a leap in protection. Body armor seeks to prevent the penetration of a projectile and dissipate its kinetic energy over a wide enough area so as not to cause impact trauma. At the same time, wearers prefer the armor that is light and comfortable. Unfortunately, comfort and protection are competing requirements. The present invention may thus provide both extremes according to user control. Materials such as Kevlar and Zylon can be woven into thin and flexible materials, with the resulting materials able to prevent penetration. However, distributing the energy of impact benefits from flexural rigidity associated with rigid ballistic inserts. The present invention may replace rigid ballistic inserts, which not only break up larger, high-velocity projectiles such as rifle bullets, but also protect the wearer from the blunt trauma injuries associated with kinetic energy transfer.

A material that can change from flexible to rigid on demand can thus be comfortable for to wear and yet afford a high degree of protection. The additional shock dissipation protection from rigidity could be enabled manually (on entering dangerous areas, for example) or automatically in response to certain stimuli. Suitable stimuli include optical or IR motion detection ("fly eye"), laser reflection, acoustic or sonic signature and magnetic or capacitive proximity sensing depending on the nature of the threat.

By modulating the stiffness and damping, the meta-material can also be protected from failure. If this modulation is done over a large deformation, then a large amount of energy can be dissipated. Thus, in addition to being able to switch the stiffness of the armor, materials with controllable properties can offer improved protection by dissipating more energy than the same mass of a fixed property material. Activation element materials may include the same materials used in existing body armor, such as ceramics in Small Arms Protective Inserts. In this case, the present invention provides penetration protection in addition to shock dissipation (another way in which the material is multifunctional).

Other applications where active control of stiffness, damping or another mechanical property are useful include: medical devices, such as endoscopes, surgical tools, vascular intervention devices such as MRI compatible stents, and arterial scraping devices; sporting equipment such as skis, racquets, clubs, athletic clothing and shoes, sails on a sail boat, and exercise equipment with variable resistance; furniture with stiffness control for comfort; home and building components such as electrostatic door locks; devices with active feedback such as keyboards and braille devices; and many applications in an automobile such as suspensions, impact absorption/crumple zones, electrostatic brakes, and seat belts.

The present invention is also suited for use in a tentacle-type robot or other long, thin reconfigurable structure. The meta-material enables the tentacle to lock into a desired position or configuration. When clamped, the meta-material increases stiffness of the tentacle. The tentacle robot may use any suitable actuator, such as one or more electric motors. In one embodiment, the tentacle employs one or more electroactive polymer actuators and a meta-material. The electroactive polymer provides for a simple and lightweight, yet highly articulated snake-like structure.

The tentacle robot may include a rolled electroactive polymer actuator disposed in a tubular meta-material (see FIGS. 2K-2L). A rolled electroactive polymer converts between electrical and mechanical energy; and includes a rolled electroactive polymer and at least two electrodes to provide the mechanical/electrical energy conversion. Rolled electroactive polymer devices allow for compact electroactive polymer device designs that can be configured to actuate in many ways including linear axial extension/contraction, bending, and multi-degree of freedom actuators that combine both extension and bending. Rolled electroactive polymers also provide a simple alternative for obtaining multilayer electroactive polymer devices. In one embodiment, a rolled electroactive polymer device employs a mechanism, such as a spring, that provides a force to strain the polymer. Further description of rolled electroactive polymer devices is included in commonly owned pending patent application Ser. No. 10/793,401, which is incorporated by reference in its entirety for all purposes.

Figure 9:
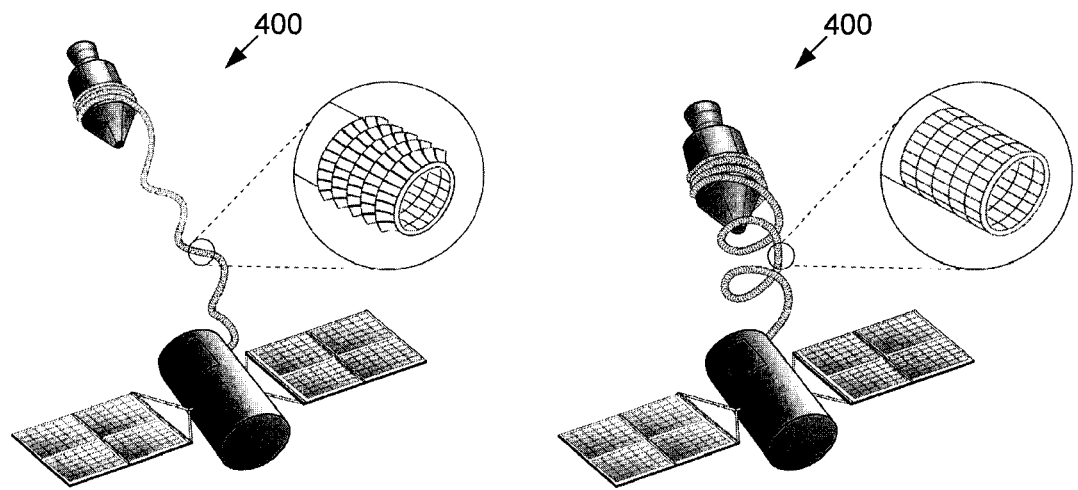
FIG. 9 illustrates a tentacle robot including a cylindrical meta-material and used in an exemplary space application.

Such a tentacle robot is scalable to various sizes and applications. The size of the tentacle may vary from millimeters to meters in length, for example. The robot may also include any number of degrees of freedom (DOF), as determined by the underlying actuation scheme. A long tentacle robot is useful, for example, with space applications and on-orbit diagnosis and repair of spacecraft (system 400 of FIG. 9). A shorter tentacle robot employing a meta-material is also well suited for use in other robotics applications, such as end-effectors, fingers, snake-like robots, etc.

Figure 10A:
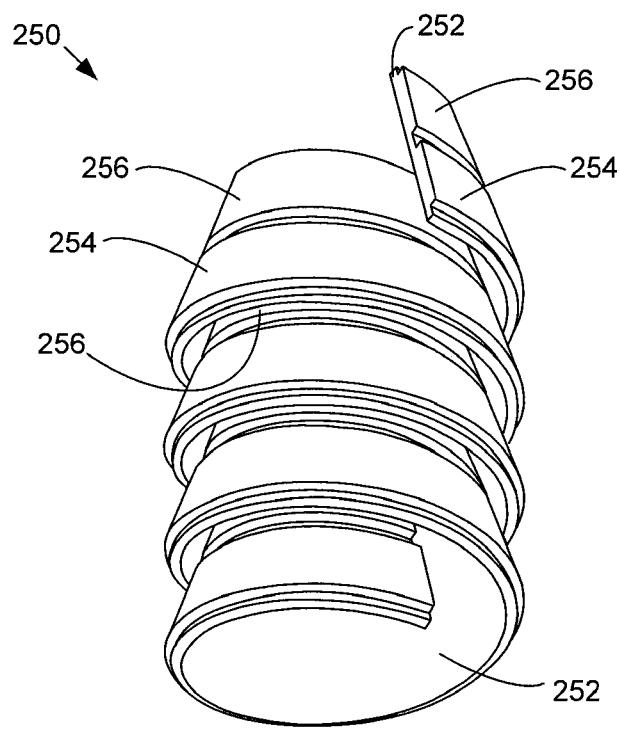
FIGS. 10A-10C illustrate three exemplary coiled meta-material designs.
Figure 10B:
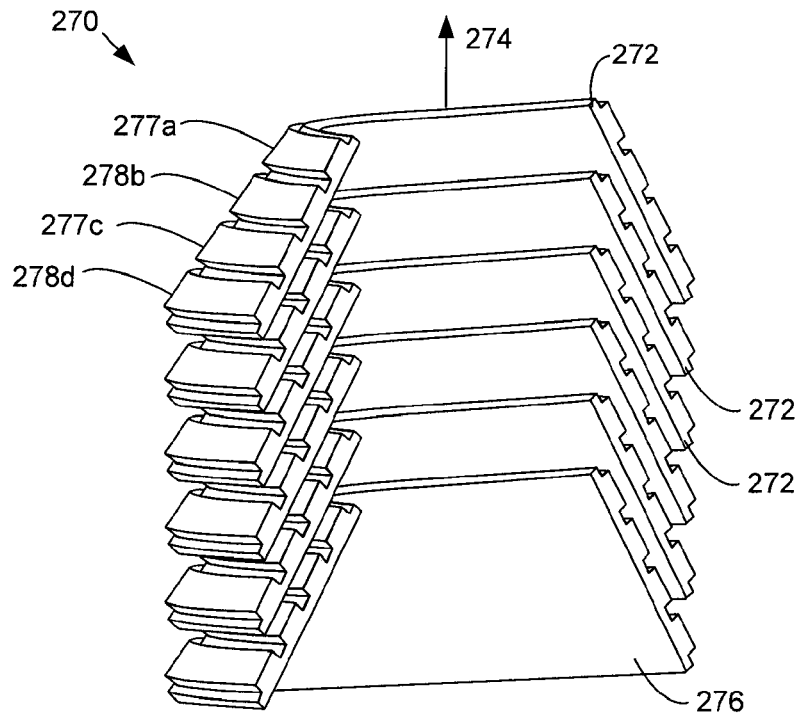
Figure 10C:
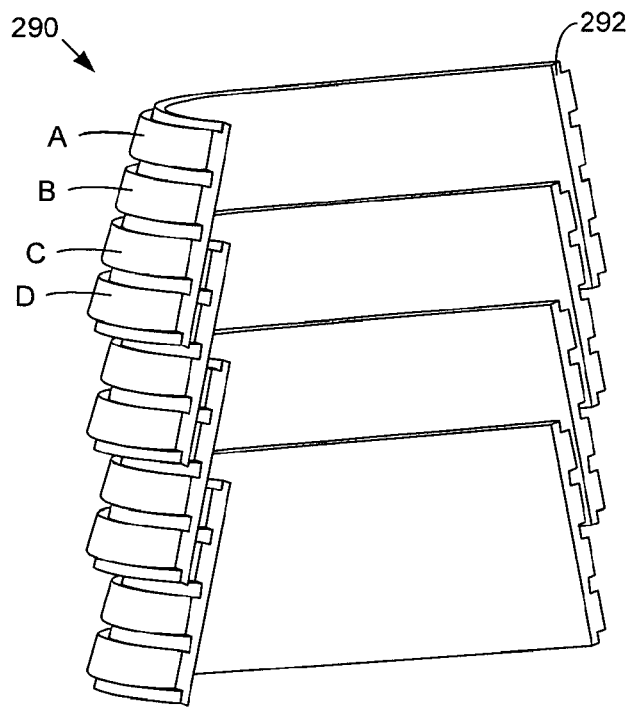

In one embodiment, the tentacle robot includes one or more spiral electrolaminate meta-material designs. FIGS. 10A-10C illustrate three exemplary spiral meta-material designs. Referring initially to FIG. 10A, a cross-sectional view of a first spiral and tubular meta-material 250 is shown.

Meta-material 250 includes an inner dielectric ribbon 252 upon which upper electrode 254 and lower electrode 256 (thickness exaggerated for both electrodes) are deposited on the same side. The coiled ribbon 252 forms a deformable structure that may bend or stretch when no electrostatic clamping voltage is applied via electrodes 254 and 256. As the ribbon 252 is coiled (in this case from the bottom to the top), the lower electrode 256 overlaps the upper electrode 254 of the previous winding. This forms one extended activation element that spirals through meta-material 250. When an electrostatic clamping voltage difference exists between the two electrodes 254 and 256, the layers of ribbon 252 are electrostatically attracted together and clamp, resulting in a substantially rigid tube. When the electrostatic clamping voltage is removed, adjacent coils may slide past one another, allowing the deformable structure to bend and/or stretch.

FIG. 10B shows a cross-sectional view of another coiled meta-material 270 in accordance with another embodiment of the present invention. Meta-material 270 includes an inner dielectric ribbon 272 overlapped along a tubular axis 274. Each coil 272 includes an insulating layer 276 and multiple electrodes 277 and 278 disposed on the outside surface of insulating layer 276. More specifically, layer 276 includes two electrodes 277*a* and 277*c* and two electrodes 278*b* and 278*d* that alternate in polarity on the surface. Electrodes 277 and electrodes 278 have a different electrical connectivity. For example, electrodes 278 may all be ground. As the layers 272 are coiled, electrode 277 on one layer 272 overlaps an electrode 278 of the other polarity on another layer 272. Electrostatic clamping voltages may be applied across insulating layer 276 using electrodes 277 and electrodes 278. By providing multiple layers 272 of electrolaminates, meta-material 270 provides a potentially stiffer and stronger tubular sheath than meta-material 250.

FIG. 10C shows a cross-sectional view of a third tubular meta-material 290 in accordance with another specific embodiment of the present invention. Meta-material 290 includes an inner dielectric ribbon 292 overlapped along a tubular axis similar to meta-material 270. In this case, however, each coil 292 includes four electrodes: A, B, C, and D. Layers 292 are coiled such that i) electrode A on one layer 292 overlaps electrode C on another layer 292, and ii) B overlaps D. As described above, by using an AC signal on multiple electrode pairs, charge accumulation in a dielectric or insulation layer can be avoided. For example, the A-C electrode pair can be energized out of phase (e.g., 90° or some other suitable time variation) with the B-D electrode pair in order to maintain at least 50% area clamping at all times.

A fourth coiled and tubular variation (not shown) uses a single electrode, and successive coils do not necessarily overlap. A second electrode is disposed on the flexible tubular or cylindrical substrate (e.g., an electrode the outermost layer of an electroactive polymer roll, similar to the design of FIG. 2F). When a voltage is applied between these two electrodes, the sheath electrostatically clamps to the flexible substrate, creating a rigid tubular structure. In one embodiment, the insulative layer between the electrodes resides on either the outside of the flexible substrate or the inside of the meta-material sheath.

There are design alternatives among these four variations. For example, a meta-material tube can have a shallow angle and many coils, or have a steep angle and very few coils. While a given length of the former would most likely have better flexibility when the electrolaminate is inactive, it might also have a lower strength due to the thinner overlap area in that region.

Another embodiment for integrating a meta-material with an electroactive polymer roll or other tubular element is a cage structure about the electroactive polymer roll. Each side of the cage may include a conductive tongue wrapped in an activation layer that slides into an out of a conductive-lined sheath. For example, each side may include a polyimide-wrapped copper tongue slides into a copper-lined sheath. De-activated, the electroactive polymer roll can bend as the tongue slides out of the sheath. If activated, the tongue is locked and prevents bending or axial extension of the electroactive polymer roll.

It is recognized that many of the previously mentioned embodiments may also be integrated with such tubular structures since they can all be formed into thin sheets or cylindrical shapes.

One advantage of the present invention is that facilitates shape change of an object that includes a meta-material. In one embodiment, the present invention de-activates activation elements and reduces stiffness of a meta-material before changing shape of the object. The object may use an actuator and/or energy from the environment to change shape. Once the new shape has been achieved, the activation elements are triggered to lock in the new shape at an increased stiffness. Such shape changing ability is useful in many applications, such as robotics and aeronautics.

While this invention has been described in terms of several preferred embodiments, there are alterations, permutations, and equivalents that fall within the scope of this invention which have been omitted for brevity's sake. For example, although the present invention has been described in terms of several specific electrode materials, the present invention is not limited to these materials and in some cases may include air as an electrode. It is therefore intended that the scope of the invention should be determined with reference to the appended claims

What is claimed is:

1. A meta-material comprising:
   a deformable or reconfigurable structure adapted to move or deform in a first lateral direction; and
   a plurality of activation elements that mechanically couple to the deformable structure and are configured to change between a first activation state and a second activation state, wherein the first activation state permits relative motion in said first lateral direction in the deformable or reconfigurable structure, and wherein the second activation state includes an electrostatic clamp that restricts relative motion in said first lateral direction in the deformable or reconfigurable structure between two of said plurality of activation elements participating in the electrostatic clamp, said electrostatic clamp providing an electrostatic force between said two activation elements that is substantially perpendicular to said first lateral direction.

2. The meta-material of claim 1, wherein said electrostatic clamp prevents relative motion in said first lateral direction until a component along said first lateral direction of an applied external force exceeds an opposing friction force along said first lateral direction caused by said electrostatic force.

3. The meta-material of claim 1, wherein the deformable structure comprises a compliant layer.

4. The meta-material of claim 1, wherein each activation element includes a stiff component having a stiffness greater than a stiffness for the deformable structure.

5. The meta-material of claim 4, wherein each activation element is bendable but not extendable along said first lateral direction.

6. The meta-material of claim 4, wherein each activation element includes an electrode disposed on one surface of the stiff component.

7. The meta-material of claim 1, wherein each activation element at least partially laterally overlaps an adjacent activation element along said first lateral direction.

8. The meta-material of claim 1, wherein a first subset of activation elements attach to a first surface of the compliant layer and a second subset of activation elements attach to a second surface of the compliant layer that is opposite to the first surface.

9. The meta-material of claim 1, wherein the meta-material includes a first shape when the at least one of the activation elements is in the first activation state and includes a second shape when the at least one of the activation elements has been activated to the second activation state.

10. The meta-material of claim 1, further comprising a locking mechanism that reduces the energy required to maintain a position of the meta-material when the at least one of the activation element has been activated to the second activation state.

11. The meta-material of claim 1, further comprising independent electrical communication with each activation element in the set of activation elements.

* * * * *